US005712247A

United States Patent [19]
Wu et al.

[11] Patent Number: 5,712,247
[45] Date of Patent: Jan. 27, 1998

[54] USE OF LACTOFERRIN TO MODULATE AND/OR NEUTRALIZE HEPARIN ACTIVITY

[75] Inventors: Hai-Feng Wu, Carrboro; Frank Clement Church, Chapel Hill, both of N.C.

[73] Assignee: University of North Carolina, Chapel Hill, N.C.

[21] Appl. No.: 391,986

[22] Filed: Feb. 21, 1995

[51] Int. Cl.$^6$ .......................... A61K 38/02; A61K 38/36; C07K 14/00; C07K 14/435
[52] U.S. Cl. .............................................. 514/12; 514/822
[58] Field of Search ........................................ 514/12, 822

[56] References Cited

U.S. PATENT DOCUMENTS 5,198,419  3/1993  Ando et al. .................................. 514/8
5,304,633  4/1994  Tomita et al. ............................. 530/326

OTHER PUBLICATIONS

Mann et al. delineation of the glycosaminoglycan–binding site in the human inflammatory response protein lactoferrin. J. Biol. Chem., 269 (38) 23661–23667, 1994.

Adeyemi, L.B. et al. "Plasma Lactoferrin and Neutrophil Elastase in Rheumatoid Arthritis and Systematic Lupus Erythematosus". British Journal of Rheumatology 29:15–20 (1990).

Adeyami, E.O. et al. "Plasma Lactoferrin as a marker of infection in elderly individuals". Aging Clin. Exp. Res. 4: 135–137 (1992).

Anderson, B.F. et al. "Apolactoferrin structure demonstrates ligand–induced conformational change in transferrins". Nature 344:784–787 (1990).

Anderson, B.F. et al. "Structure of Human Lactoferrin: Crystallographic Structure Analysis and refinement at 2.8 A Resolution". J. Mol. Biol. 209:711–734 (1989).

Bick, R.L. and Ucar, K. "Hypercoagulability and Thrombosis". Hematology/Oncology Clinics of North America 6(6):1421–1431 (1992).

Bick, R.L. "Disseminated Intravascular Coagulation and Related Syndromes: A Clinical Review". Seminars in Thrombosis and Hemostasis 14(4):299–338 (1988).

Blackberg, L. and Hernell, O. "Isolation of Lactoferrin From Human Whey by a Single Chromatographic Step". Elsevier/Morth–Holland Biomedical Press 109(2):180–184 (1980).

Broze, G.J. et al. "Regulation of Coagulation by a Multivalent Kunitz–Type Inhibitor". American Chemical Society 29(33):7539–7546 (1990).

Carp H. and Janoff A., "Modulation of Inflammatory Cell Protease–Tissue Antiprotease Interactions at Sites of Inflammation by Leukocyte–derived Oxidants". In Advances in Inflammation Research, vol.5, G. Weissmann (ed.), Raven Press, New York, 1983. pp. 173–201.

Day, C.L. et al. "Structure of the Recombinant N–Terminal Lobe of Human Lactoferrin at 2.0 A Resolution". J. Mol. Biol. 232:1084–1100 (1993).

Day, C.L. et al. "Studies of the N–terminal Half of Human Lactoferrin Produced from the cloned cDNA Demonstrate That Interlobe Interactions Modulate Iron Release". Journal of Biological Chemistry 267(20):13857–13862 (1992).

de Agostini, A.I. et al. "Localization of Anticoagulantly Active Heparan Sulfate Proteoglycans in Vascular Endothelium: Antithrombin Binding on Cultured Endothelial Cells and Perfused Rat Aorta". Journal of Cell Biology 111:1293–1304 (1990).

Esmon, C.T. "The Protein C Anticoagulant Pathway". Arteriosclerosis and Thrombosis 12(2):135–145 (1992).

Furie, B. and Furie, B.C. "Molecular and Cellular Biology of Blood Coagulation". New England Journal of Medicine 326(12):800–806 (1992).

Gewirtz, A.M. et al. "Inhibition of Human Megakaryocytopoiesis In Vitro by Platelet Factor 4 (PF4) and a Synthtic COOH–Terminal PF4 Peptide". J. Clin. Invest. 83:1477–1486 (1989).

Griffith, M.J. et al. "Reactive Site Peptide Structural Similarity between Heparin Cofactor II and Antithrombin III". Journal Of Biological Chemistry 260(4):2218–2225 (1985).

Han, Z.C. et al. "Platelet Factor 4 Inhibits Human Megakaryocytopoiesis In Vitro". Blood 75(6):1234–1239 (1990).

Herion, J.C. et al. "Isolation and Characterization of granulocyte Lyosomal Proteins and Study of Their Effects on the Clotting System". American Journal of Hematology 7:265–279 (1979).

Horn, R.G. and Collins, R.D. "Studies on the Pathogenesis of the Generalized Shwartzman Reaction". Laboratory Investigation 18(2):101–107 (1968).

Horrow, J.C. "Protamine: A Review of its Toxicity". Anesth. Analg. 64:348–361 (1985).

Iyer, S. and Lönnerdal, B. "Lactoferrin, lactoferrin receptors and iron metabolism". European Journal of Clinical Nutrition 47:232–241 (1993).

Johnson, D. and Travis, J. "The Oxidative Inactivation of Human α–1–Proteinase Inhibitor". Journal of Biological Chemistry 254(10):4022–4026 (1979).

Just–Vierra, J.O. et al. "Acute Reaction to Protamine". The American Surgeon 50(1):52–60 (1984).

Primary Examiner—Cecilia J. Tsang
Assistant Examiner—Michael Borin
Attorney, Agent, or Firm—Myers Bigel Sibley & Sajovec, LLP

[57] ABSTRACT

A method for modulating, regulating and/or neutralizing heparin-dependent anticoagulant reactions by administration of lactoferrin or polypetide fragments thereof. Said method may be used to correct the "heparin-induced" prolongation of blood coagulation and other coagulapathies in cardiopulmonary bypass, cardiac catheterization and hemodialysis patients. Said method may further be used to treat disorders and diseases related to unregulated or unmodulated heparin activity. Said method of treatment is comprised of administration of lactoferrin or fragments thereof comprised of the heparin binding domain(s) of lactoferrin.

8 Claims, 10 Drawing Sheets

OTHER PUBLICATIONS

Kalmar, J.R. et al. "Superior leukocyte separation with a discontinuous one-step Ficoll–Hypaque gradient for the isolation of human neutrophils". *Journal of Immunological Methods* 110:275–281 (1988).

Katz, L.R. et al. "Protease-induced immunoregulatory activity of platelet factor 4". *Proc. Natl. Acad. Sci. USA* 83:3491–3495 (1986).

Koivuranta-Vaara, P. et al. "Bacterial-Lipopolysaccharide-Induced release of Lactoferrin from Human Polymorphonuclear Leukocytes: Role of Monocyte-Derived Tumor Necrosis Factor $\alpha$". *Infection and Immunity* 55(12):2956–2961 (1987).

Lane, D.A. et al. "Neutralization of Haparin–related Saccharides by Histidine–rich Glycoprotein and Platelet Factor 4". *Journal of Biological Chemistry* 261(9):3980–3986 (1986).

Lash, J.A. et al. "Plasma Lactoferrin Reflects Granulocyte Activation In Vivo". *Blood* 61(5):885–888 (1983).

Lassiter, M.O. et al. "Characterization of Lactoferrin Interaction with Streptococcus Mutants". *J Dent Res* 66(2):480–485 (1987).

Lonky, S.A. et al. "Stimulation of Human Granulocyte Elastase by Platelet Factor 4 and Heparin". *Biochemical and Biophysical Research Communications* 85(3):1113–1118 (1978).

Loscalzo, J. et al. "The Interaction of Platelet Factor Four and Glycosaminoglycans". *Archives of Biochemistry and Biophysics* 240(1):446–455 (1985).

Lundblad, R.L. "A Rapid Method for the Purification of Bovine thrombin and the Inhibition of the Purified Enzyme with Phenylmethylsulfonyl Fluoride". *Biochemistry* 10(13):2501–2505 (1971).

Maione, T.E. et al. "Inhibition of Tumor Growth in Mice by an Analogue of Platelet Factor 4 That Lacks Affinity for Heparin and Retains Potent Angiostatic Activity". *Cancer Research* 51:2077–2083 (1991).

Maione, T.E. et al. "Inhibition of Angiogenesis by Recombinant Human Platelet Factor–4 and Related Peptides". *Science* 247:77–79 (1990).

Mann, D.M. "The Glycosaminoglycan Binding Site in the Inflammatory Response Protein Lactoferrin". *FASEB Journal* 8: Abstract #5176. date not available.

Marcum, J.A. and Rosenberg, R.D. "Anticoagulantly Active Heparan Sulfate Proteoglycan and the Vascular Endothelium". *Seminars in Thrombosis and Hemostasis* 13(4):464–474 (1987).

Masson, P.L. et al. "Lactoferrin, An Iron–Binding Protein NI Neutrophilic Leukocytes". *J. Exp. Med.* 130:643. 1970.

McGuire, E.A. and Tollefsen, D.M. "Activation of Heparin Cofactor II by Fibroblasts and Vascular Smooth Muscle Cells". *Journal of Biological Chemistry* 262(1):169–175 (1987).

McKay, D.G. and Shapiro, S.S. "Alterations in the Blood Coagulation System Induced by Bacterial Endotoxin". *J. Exp. Med.* 107:353. 1958.

Mertens, G. et al. "Cell Surface Heparan Sulfate Proteoglycans from Human Vascular Endothelial Cells". *Journal of Biological Chemistry* 267(28):20435–20443 (1992).

Metz–Boutigue, M.H. et al. "Human Lactotransferrin: amino acid sequence and structural comparisons with other transferrins". *Eur. J. Biochem.* 145:659–676 (1984).

Niwa, M. et al. "Histidine–Rich Glycoprotein Inhibits the Antithrombin Activity of Heparin Cofactor II in the Presence of Heparin or Dermatan Sulfate". *Thrombosis Research* 37:237–240 (1985).

Nuijens, J.H. et al. "Plasma elastase $\alpha_1$–antitrypsin and lactoferrin in sepsis: Evidence for neutrophils as mediators in fatal sepsis". *J. Lab Clin. Med.* 119(2):159–168 (1992).

Olson, S.T. and Bjork I. "Regulation of Thrombin by Antithrombin and Heparin Cofactor II". In *Thrombin: Structure and Function*. Berliner ed, 1992, Plenum Press, New York, NY. pp. 159–217.

Palma, C. et al. "Lactoferrin Release and Interleukin–1, Interleukin–6, and Tumor Necrosis Factor Production by Human Polymorphonuclear Cells Stimulated by Various Lipopolysaccharides: Relationship to Growth Inhibition of Candida albicans" *Infection and Immunity* 60(1):4604–4611 (1992).

Parker, R.I. et al. "Absence of the largest Platelet–von Willebrand Multimers in a Patient with Lactoferrin Deficiency and a Bleeding Tendency". *Thrombosis and Haemostasis* 67(3):320–324 (1992).

Powell, M.J. and Ogden, J.E. "Nucleotide sequence of human lactoferrin cDNA". *Nucleic Acids Research* 18(13):4013 (1990).

Pratt, C.W. and Church, F.C. "Antithrombin: Structure and Function". *Seminars in Hematology* 28(1):3–9 (1991).

Pratt, C.W. and Church, F.C. "General features of the heparin–binding serpins antithrombin, heparin cofactor II and protein C inhibitor". *Blood Coagulation and Fibrinolysis* 4:479–490 (1993).

Rosenberg, R.D. and Damus, P.S. "The Purification and Mechanism of Action of Human Antithrombin–Heparin Cofactor". *Journal of Biological Chemistry* 248(18):6490–6505 (1973).

Roberts, H. and Lozier, J. "New Perspectives on the Coagulation Cascade". *Hospital Practice*:97–112 (Jan. 15, 1992).

Rosenberg, R.D. et al. "Structure–function relationships of heparin species". *Proc. Natl. Acad. Sci. USA* 75(7):3065–3069 (1978).

Saba, H.I. et al. "Anti–Heparin Activity of Lysosomal Cationic Proteins from Polymorphonuclear Leukocytes". *Blood* 31(3):369–380 (1968).

Sadler, J.E. et al. "Structure–Function Relationships of the Thrombin–Thrombomodulin Interaction". *Haemostasis* 23(suppl 1):183–193 (1993).

Slungaard, A. and Key, N.S. "Platelet Factor 4 Stimulates Thrombomodulin Protein C–activating Cofactor Activity". *Journal of Biological Chemistry* 269(41):25549–25556 (1994).

Spero, J.A. et al. "Disseminated Intravascular Coagulation". *Thrombo. Haemost.* 42:28. 1979.

Tollefsen, D.M. and Pestka, C.A. "Modulation of Heparin Cofactor II Activity by Histidine–rich Glycoprotein and Platelet Factor 4". *Journal of Clinical Investigation* 75:496. 1985.

Van Deerlin, V. and Tollefsen, D.M. "The N–terminal Acidic doamin of Heparin Cofactor II Mediates the Inhibition of $\alpha$–Thrombin in the Presence of Glycosaminoglycans". *Journal of Biological Chemistry* 266(30):20223–20231 (1991).

Whinna, H.C. et al. "Interaction of Heparin Cofactor II with Biglycan and Decorin". *Journal of Biological Chemistry* 268(6):3920–3924 (1993).

Zou, S. et al. "Heparin–Binding Properties of Lactoferrin and Lysozyme". *Comp. Biochem. Physiol.* 103B(4):889–895 (1992).

Zucker, M.B. et al. "Immunoregulatory activity of peptides related to platelet factor 4". *Proc. Natl. Acad. USA* 86:7571–7474 (1989).

USE OF LACTOFERRIN TO MODULATE AND/OR NEUTRALIZE HEPARIN ACTIVITY

This work was supported in part by Research Grant HL-32656 from the National Institutes of Health and a Grant-in-Aid from the American Heart Association.

INTRODUCTION

The present invention is directed to the novel use of lactoferrin and polypeptide fragments thereof to neutralize the activity of heparin and pharmaceutical formulations regarding the same. More specifically, the invention is directed to polypeptides comprising the heparin binding domain of lactoferrin for use as a heparin neutralizer.

BACKGROUND OF THE INVENTION

Blood coagulation is a host defense system which maintains the integrity of the circulatory system. Roberts and Lozier, 1992, Hosp. Pract. 97; Furie and Furie, 1992, N. Engl. J. Med. 326:800. In this process, thrombin serves as a critical factor by activating platelets and factors V and VIII, and clotting fibrinogen. Following its formation, thrombin is regulated by various anticoagulant pathways. See e.g., Broze et al., 1990, Biochemistry 29:7539; Esmon, 1992, Arterioscl. Thromb. 12:135; Olson, 1992, "Regulation of thrombin by antithrombin and heparin cofactor II," Thrombin: Structure and Function, Plenum Press, New York, N.Y.; Pratt and Church, 1991, Sem. Hematol. 28:3; Rosenberg et al., 1978, Proc. Natl. Acad. Sci. USA 75:3065; and Sadler et al., 1993, Haemostasis 23(suppl):183. One such pathway is the inhibition of thrombin by the plasma serpins (serine proteinase inhibitors) antithrombin and heparin cofactor II. The thrombin-inhibiting activity of both of these serpins is greatly accelerated in the presence of glycosaminoglycans such as heparin, an anticoagulant polysaccharide that in conjunction with these serpins, forms an inactive complex antiprothrombin. Rosenberg and Damus, 1973, J. Biol. Chem. 248:6490; Pratt and Church, 1993, Blood Coag. Fibrinol. 4:479.

A patient receiving cardiopulmonary bypass, cardiac catheterization, and hemodialysis is administered heparin when undergoing such surgical procedures to "thin" the patient's blood. A second compound is typically then administered following completion of the surgical procedure to neutralize the heparin. Protamine sulfate, a highly basic protein obtained from salmon sperm, is widely used for this purpose. However, the use of protamine sulfate has shown to result in several adverse reactions including urticaria, flushing, leukopenia, thrombocytopenia, bronchospasm, elevated pulmonary arterial pressure, pulmonary edema. Horrow, 1985, Anesth. Analg. 64:348–361; Holland et al., 1984, Clin. Cardiol. 7:157–162; Schapira and Christman, 1990, Circulation 82: 1877–79. Occasionally, the patients receiving protamine sulfate suffered from systemic hypotension which may lead to cardiovascular collapse and death. Just-Viera et al., 1985, Am. Surg. 50:52–60; Weiss et al., 1989, N. Engl. J. Med. 320:886–892. The toxic effects of protamine sulfate are likely due to a formation of heparin/protamine sulfate complex which activate complementary systems and initiate an abnormal immunoresponse. The incidence of mild reactions to the use of protamine sulfate is as high as 16% and that of severe reactions is between 0.2% and 3%. Holland et al., 1984, Clin. Cardiol. 7:157–162; Cook et al., 1992, Circulation 85:1102–09. In addition, subtle pathological effects of protamine may go unnoticed and contribute to postoperational morbidity and mortality. Therefore, a substitution of protamine sulfate with a molecules without those adverse effects has been a major clinical issue.

To date, available alternatives to protamine sulfate have also proven problematic. For example, platelet factor 4 has been suggested as a potential drug to neutralize heparin. However, in addition to the neutralization of heparin platelet factor 4 also regulate other biological processes such as inhibition of angiogenesis and endothelial cell proliferation, promotion of inflammatory damage through elastin proteolysis, modulation of host immunoreactivity, and enhancement of thrombomodulin anticoagulant function. See e.g., Horrow, 1985, Anesth. Analg. 64:348–361; Just-Viera et al., 1985, Am. Surg. 50:52–60; Maione et al., 1990, Science 247:77–79. These activities of platelet factor 4 potentially present a major hindrance of its clinical application.

Lactoferrin is an iron-binding protein closely related in structure to the serum iron transporting protein, transferrin. The amino acid sequence identity between these proteins is more than 55%. Iyer and Lonnerdal, 1993, Eur. J. Clin. Nutr. 47:232. Lactoferrin is a single polypeptide chain of 692 residues containing an internal repeat, with the amino-terminal half about 40 % identical with the carboxyl-terminal half. Masson et al., 1969, J. Exp. Med. 130:643. Each half of the lactoferrin molecule has a single iron binding site with a Kd of ~10–20M. Human lactoferrin is found in milk, tears, saliva, and it is also a prominent component of secondary granules of neutrophils. Iyer and Lonnerdal, 1993, Eur. J. Clin. Nutr. 47:232; Masson et al., 1969, J. Exp. Med. 130:643. Although lactoferrin is a natural blood component derived from neutrophil secondary granules and its ability to bind to heparin has been partially characterized, lactoferrin's physiological role in the regulation of inflammation and other host defense mechanisms remains unclear. See e.g., Lash et al., 1983, Blood 61:885; Blackberg et al., 1980, FEBS Letters 109:180; Zou et al., 1992, Comp. Biochem. Physiol. 103:889. The N-terminus of lactoferrin contains heparin-binding consensus sequences (BBXB or BXXBBXB, where B is a basic residue and X is any residue). However, lactoferrin and particularly the N-terminus region of lactoferrin has not been considered a tool for use in regulating, modulating and/or neutralizing heparin activity.

SUMMARY OF THE INVENTION

As discovered by the present inventors, lactoferrin and polypeptide fragments thereof may be used to neutralize and/or regulate the activity of heparin, a known anticoagulant principle. The present invention is therefore directed to the use of lactoferrin to regulate blood coagulation by inhibiting and/or regulating anticoagulant activity, including the neutralization of heparin in the patients undergoing cardiovascular surgery and other surgical procedures by modulating heparin-serpin and/or heparin thrombin interactions. The present invention is further directed to the use of lactoferrin to regulate and/or inhibit heparin-dependent activities, including for example the antithrombin-thrombin inhibition reaction, prolongation of blood plasma coagulation and thrombotic complications associated with inflammatory diseases. The present invention is further directed to the treatment of disorders and/or diseases associated with blood coagulation and more specifically to disorders and/or diseases related to the unregulated activity of heparin.

The present invention is also directed to pharmaceutical formulations and compositions comprised of lactoferrin or polypeptide fragments thereof used in the treatment of the diseases, disorders and mechanisms described above. More specifically, the invention is directed to pharmaceutical compositions and formulations comprising the binding domain(s) along the lactoferrin molecule responsible for heparin neutralization effects, such as the domain along the N-terminus (residues 1–61) of lactoferrin.

DESCRIPTION OF THE FIGURES AND DRAWINGS

FIG. 1 sets forth data related to the neutralization of heparin by lactoferrin measured in an antithrombin-thrombin inhibition reaction. Data related to lactoferrin is designated (●), lactoferrin-EDTA (○), hololactoferrin (Δ), neutrophil lactoferrin (▲), platelet factor 4 (□), protamine sulfate (■), transferrin (X) and lactoferrin-Ab (+).

FIG. 2 sets forth evidence regarding the neutralization of heparin by lactoferrin measured in a heparin cofactor II-thrombin inhibition reaction. Data related to lactoferrin is designated (●), hololactoferrin (○), protamine sulfate (Δ), neutrophil lactoferrin (▲) and platelet factor 4 (□).

FIGS. 3A–C provide evidence regarding the neutralization of heparin by neutrophil-releasing products measured in an antithrombin-thrombin inhibition reaction.

FIG. 4 sets forth data related to the dose-response effect of lactoferrin on the aPTT in heparinized plasma.

FIGS. 5A–B provide a quantitation of plasma lactoferrin obtained from whole blood after treatment with various concentrations of LPS.

FIGS. 6A–C set forth the relationship between plasma lactoferrin and platelet factor 4 levels with aPTT values of heparinized plasma obtained from whole blood treated with various agonists.

FIG. 7 sets forth data related to the effect of lactoferrin on glycosaminoglycan-catalyzed thrombin-serpin inhibition reactions. FIG. 7A reflects heparin-catalyzed thrombin inhibition by antithrombin wherein the lactoferrin concentration was 0.1 µM. FIG. 7B reflects heparan sulfate-catalyzed thrombin inhibition by antithrombin wherein the concentration of lactoferrin was 0.2 µM. FIG. 7C reflects dermatan sulfate-catalyzed thrombin inhibition by heparin co-factor II wherein the concentration of lactoferrin was 0.5 µM. For FIGS. 7A, 7B and 7c, (○) indicates control and (▲) indicates lactoferrin.

FIG. 8A and 8B reflect the kinetics of the heparin-catalyzed thrombin-antithrombin reaction. For FIGS. 8A and 8B, (○) indicates control and (▲) indicates lactoferrin.

FIG. 9 (A and B) reflects the purification of heparin binding peptides derived from proteolysis of lactoferrin with $V_8$ protease.

FIG. 10 sets forth data related to the neutralization of glycosaminoglycans by lactoferrin and lactoferrin peptides in thrombin-serpin reactions. The data is presented to show the extent of glycosaminoglycan neutralization plotted against the molar ratio of lactoferrin or lactoferrin peptide to glycosaminoglycan in the reaction. For FIGS. 10A and 10B, data related to heparin is designated (○), heparan sulfate (▲) and dermatan sulfate (●).

DETAILED DESCRIPTION OF THE INVENTION

Figure 1:
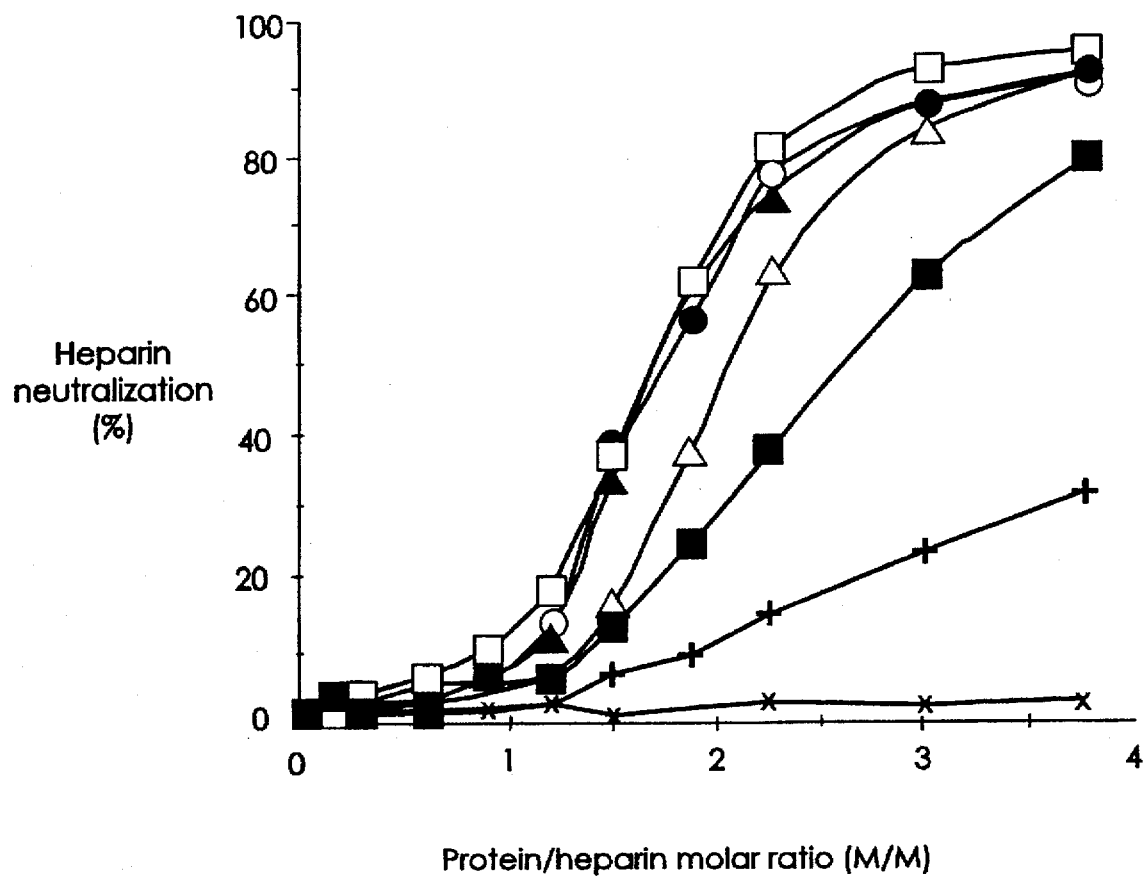

The present invention is directed to the Applicants' discovery that lactoferrin has a potent heparin-neutralizing activity during thrombin inhibition by the serine proteinase inhibitors (serpins) antithrombin and heparin cofactor II. This discovery is based, in part, on the Applicants' observation that activated neutrophil supernatant containing lactoferrin can partially neutralize the heparin-dependent antithrombin-thrombin inhibition reaction. The activity of lactoferrin as a heparin-neutralizing agent is also supported by the Applicants' observation that addition of lactoferrin to plasma corrected the "heparin-induced" prolongation of blood plasma coagulation as measured by the activated partial thromboplastin time (aPTT) and that treatment of whole blood with specific inflammatory mediators, formyl-Met-Leu-Phe (fMLP), lipopolysaccharide (LPS), and tumor necrosis factor-α (TNF-α), increased the concentration of both plasma lactoferrin and platelet factor 4 while inhibiting the blood anticoagulant activity of heparin as measured by the aPTT. These results appears dose dependent wherein the higher the lactoferrin/heparin molar ratio, the higher the percentage of heparin neutralized. Such results also teach that lactoferrin may play an important physiological role in the neutralization of glycosaminoglycan-dependent serpin-thrombin inhibition reactions.

The present invention is therefore directed to the clinical application of lactoferrin and polypeptide fragments thereof, including a fragment comprised of the N-terminus (residue 1 to 61) of lactoferrin, to neutralize heparin and its derivatives and/or modulate and regulate heparin-serpin and/or heparin thrombin interactions. Specifically, intact lactoferrin and polypeptide fragments thereof may be used to neutralize heparin and thus treat, among others, patients undergoing cardiovascular surgery and other surgical procedures and other coagulopathies due to the toxicity of heparin and other glycosaminoglycans.

Production Of Lactoferrin. The lactoferrin of the present invention may be obtained from any relevant process, including purification of product from natural sources, protein synthesis and recombinant production. For example, lactoferrin can be purified from milk, generated by the recombinant DNA technology or by a transgenic cow or pig designed to produce human lactoferrin. Polypeptide fragments of lactoferrin may be made by limited proteolysis, peptide synthesis and recombinant DNA technology.

The preferred embodiment is directed to pharmaceutical compositions and methods wherein a recombinantly manufactured lactoferrin is utilized. Efficient and economical methods for producing recombinant lactoferrin or polypeptide fragments thereof have been developed recently. The cDNA sequence encoding human lactoferrin can be used to prepare recombinant human lactoferrin, thus making available a source of protein for therapeutic and nutritional applications. The confirmed cDNA sequence can be used in an appropriate cloning vehicle to replicate the cDNA sequence. Also, the cDNA can be incorporated into a vector system for human lactoferrin production. Other lactoferrin DNA sequences can be substituted for the human lactoferrin cDNA sequence to provide bovine, porcine, equine or lactoferrin from other species. Partial cDNA sequences can also be employed to give desired lactoferrin derived polypeptides. Such lactoferrin derived polypeptides are not available by enzymatic digestion of naturally occurring lactoferrin. They are free of lactoperoxidase, lysozyme or other proteins that are contaminants of lactoferrin isolated from milk or other natural sources.

Lactoferrin may be produced in a variety of different organisms which permit integration of a vector comprising the lactoferrin cDNA or fragments thereof and the expression of such cDNA. Appropriate organisms include various fungi, such as *Saccharomyces cerevisiae, Aspergillus nidulans, Aspergillus oryzae, Kluyveromyces lectis* and

*Pichia pastorsis*, insect cells such as SF9, bacterial cells and mammalian cells such as Cos cells. The preferred host for expression of multigram quantities of recombinant lactoferrin is a eukaryotic cell.

Pharmaceutical Formulations And Routes Of Administration. Lactoferrin may also be administered to a patient, by itself, or in pharmaceutical compositions where it is mixed with suitable carriers or excipient(s) at doses to treat or ameliorate a variety of diseases and disorders by neutralizing heparin activity and/or modulating and/or regulating heparin-serpin and/or heparin thrombin interactions. A therapeutically effective dose further refers to that amount of the compound sufficient to neutralize heparin activity. Techniques for formulation and administration of the compounds of the instant application may be found in "Remington's Pharmaceutical Sciences," Mack Publishing Co., Easton, Pa., latest edition.

Suitable routes of administration may, for example, include oral, rectal, transmucosal, topical or intestinal administration; parenteral delivery, including intramuscular, subcutaneous, intramedullary injections, as well as intrathecal, direct intraventricular, intravenous, intraperitoneal, intranasal, or intraocular injections. Alternately, one may administer the compound in a local rather than systemic manner, for example, in a depot or sustained release formulation.

The pharmaceutical compositions of the present invention may be manufactured in a manner that is itself known, e.g. , by means of conventional mixing, dissolving, granulating, dragee-making, levigating, emulsifying, encapsulating, entrapping or lyophilizing processes. Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For the preferred oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered mount. Capsules and cartridges of e.g. gelatin for use in an inhaler or insufflator may be formulated containing a powder mix of the compound and a suitable powder base such as lactose or starch. Administration by inhalation may also include inhalation of dry aerosols.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. Certain organic solvents such as DMSO also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 as determined in cell culture. Such information can be used to more accurately determine useful doses in humans. A therapeutically effective dose refers to that amount of the compound that results in the prevention of infection, amelioration of symptoms, or a prolongation of survival in a patient. Toxicity and therapeutic efficacy of such compounds can be determined by standard pharmaceutical procedures in cell cultures or experimental animals, e.g., for determining the LD50 (the dose lethal to 50 % of the population) and the ED50 (the dose therapeutically effective in 50 % of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p1).

The amount of composition administered will, of course, be dependent on the subject being treated, on the subject's weight, the subject's muscosal surface area, the severity of the affliction, the manner of administration and the judgment of the prescribing physician.

The compositions may, if desired, be presented in a pack or dispenser device which may contain one or more unit dosage forms containing the active ingredient or other compounds to be administered in combination with the composition. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of diseases and disorders by neutralization of heparin activity.

EXAMPLE

The Role Of Glycos aminoglycan Neutralization By Neutrophil-Derived Lactoferrin In The Regulation Of Blood Coagulation Materials And Methods Materials. All chemicals used were from Sigma Chemical Co. (St. Louis, Mo.) unless otherwise indicated, and were of the highest grade purity available. Ficoll-Hypaque Monopoly medium, collagen and polyclonal antibody against human lactoferrin conjugated with alkaline phosphatase were obtained from ICN Biochemicals (Costa Mesa, Calif.); TNF-$\alpha$, phorbol 12-myristate-13-acetate (PMA), N-tosyl-phenylalanine chloromethyl ketone (TPCK), and purified human neutrophil elastase were from CalBiochem (San Diego, Calif.); transforming growth factor-$\beta$ (TGF-$\beta$) was obtained from R & D systems Inc. (Minneapolis, Minn.); platelet factor 4 (40 kD) and a polyclonal antibody against platelet factor 4 were obtained from American Diagnostic Inc. (Greenwich, Conn.); polyclonal antibody against human neutrophil elastase was from Biodesign (Kermebunk, Me.); Polybrene was from Aldrich Chemical Co. (Milwaukee, Wis.); Na-p-tosyl-Gly-Pro-Arg-p-nitroanilide was from Boehringer-Mannheim (Indianapolis, Ind.); aPTT reagents were obtained from Pacific Hemostasis (Ventura, Calif.); heparin with an average molecular weight of 15 kD was provided from Diosynth (Oss, the Netherlands); human a-thrombin, antithrombin and heparin cofactor II were purified as described in Lundblad, 1971, *Biochemistry* 10:2501 and Griffith et al., 1985, *J. Biol. Chem.* 260:2218.

Purification of Lactoferrin. Human milk lactoferrin was purified from fresh mature milk as described by Blackberg et al., 1980, *FEBS Letters* 109:180. Human neutrophil lactoferrin was prepared as follow: 150 mL of blood was drawn from a healthy volunteer with EDTA as an anticoagulant. Neutrophils were isolated using the modified Ficoll-Hypaque gradient as described by Kalmar et al., 1988, *J. Immunol. Meth.* 110:27532. The granulocyte fraction obtained was composed of greater than 95% polymorphonuclear leukocytes, and it exhibited more than 99% cell viability as determined by trypan blue exclusion. After washing twice with Hanks Balanced Salt Solution (HBSS) without Ca++ and Mg++, the neutrophils were suspended in HBSS at $5 \times 10^6$ cells per mL and treated with 100 ng/mL PMA for 30 minutes at room temperature. After centrifugation at 2000 rpm for 5 minutes, the supernatant was collected and stored at −20° C. for further use. Neutrophil supernatants obtained from ten normal donors were loaded onto a heparin-Sepharose column (2 cm×15 cm). After initial washing with 20 mM Hepes containing 200 mM NaCl, pH 7.4, bound proteins were eluted by NaCl gradient (200–800 mM). The protein in each fraction was analyzed by sodium dodecyl sulfate-polyacrylamide gel electrophoresis and by immuno-blot analysis.

Neutrophil lactoferrin was eluted from heparin-Sepharose at the same NaCl concentration (0.6M) as that of milk lactoferrin. Approximately 50 mg of lactoferrin was purified from neutrophils obtained from one liter of blood (ten donors). The purity of both milk and neutrophil lactoferrin was evaluated using a 10% acrylamide gel with Coomassie Brilliant blue (R-250) staining. A single protein band at 80 kD was observed in both preparations. Immuno-blot analysis of both milk- and neutrophil-purified lactoferrin with a polyclonal antibody against human lactoferrin demonstrated strong immunoreactivity with the same 80 KD band. Purified iron-saturated human lactoferrin was obtained from Sigma and contained greater than 0.15% (w/w) of iron according to the manufacturer's specifications. Iron-free lactoferrin was prepared from purified milk lactoferrin as described by Lassiter et al., 1987, *J. Dent. Res.* 66:480.

Thrombin Inhibition Assay. The assay was performed in 96-well U-bottom microplates (Becton Dickinson) in 100 μL of 0.15M NaCl, 0.02M Hepes, 1 mg/mL polyethylene glycol (Mr=8000) and 1 mg/mL bovine serum albumin (BSA), pH 7.4. Inhibition reaction mixtures contained 0.1 μg/mL heparin, 50 nM serpin and various concentrations of lactoferrin or other heparin neutralizing molecules. The reaction was initiated by adding thrombin (5 nM) to the microplate well. After an incubation of 30–40 seconds, 50 μL of a solution containing 0.2 mM tosyl-Gly-Pro-Arg-p-nitroanilide and 1.5 mg/mL Polybrene was added. Residual thrombin activity was determined by measuring the hydrolysis of the chromogenic substrate in a Molecular Devices Vmax kinetic microplate reader. All thrombin inhibition assays were performed at least three times and mean values of heparin neutralization and standard deviation were determined. Percentage of heparin neutralization is expressed by plotting extent of neutralization of anticoagulant activity against the molar ratio of neutralizing protein/heparin. Heparin neutralization % was calculated as follows: heparin neutralization %=[(B−A)/(C−A)]×100%; where A is the thrombin residual activity obtained at presence of serpin and heparin; B is the activity obtained in the presence of serpin, heparin and lactoferrin or other indicated molecules; and C is the activity obtained in the presence of serpin only. Control experiments verified that lactoferrin did not affect: (1) the activity of thrombin alone, (2) the activity of thrombin in the presence of heparin, (3) and the thrombin inhibition by the serpins in the absence of heparin.

Preparation of Neutrophil-Releasing Products. Human neutrophils were isolated from venous blood (anticoagulated with EDTA) by centrifugation on Ficoll-Hypaque gradient as described above. The isolated neutrophils were then washed twice with HBSS and suspended in the same solution at a density of 5–10×$10^6$ cells per mL. 300 μL cell suspension was incubated with various agonists at the indicated concentrations for 30 minutes at 37° C. Incubation was terminated by centrifugation at 2000 rpm for 5 minutes. The cell-free supernatants were collected and stored at −20° C. until assayed.

Enzyme-linked Immunosorbent Assay (ELISA). The concentration of lactoferrin in both plasma and neutrophil supernatants was determined by a double-sandwich ELISA. Briefly, microplate wells were coated with 100 μL of rabbit polyclonal antibody against human purified lactoferrin (Cappel-Organon Teknika Corp.) at a 1:500 dilution at 4° C. overnight. The plate was then washed twice with phosphate-buffered saline (PBS) containing 0.05% Tween 20 and 0.5M NaCl, pH 7.5 (washing buffer). After blocking with 1% BSA in PBS for 2 hours, a neutrophil supernatant dilution of 1:200 or a plasma dilution of 1:20 in blocking solution containing 0.05% Tween 20 (incubation buffer) was added to the wells in 100 mL volume. Following incubation for 2 hours at room temperature, the plate was washed twice with washing buffer. Rabbit anti-human lactoferrin antibody conjugated with alkaline phosphatase at a dilution of 1:5000 was then added for one hour. Finally, the plate was washed four times with washing buffer and 100 μL substrate containing 1 mg/mL p-nitrophenyl-phosphate in 10 mM diethanolamine, 0.5 mM MgCl2, pH 9.5 was added. Substrate hydrolysis was measured kinetically in the microplate reader at 405 nM. Alkaline phosphatase activity in each well was determined as mOD/min.

The concentration of elastase in activated neutrophil supernatants was measured by a direct ELISA. Microplate wells were coated with the various neutrophil supernatants in PBS at 4° C. overnight. After treatment with the washing buffer, the wells were blocked with 2% BSA/PBS for 2 hours at 37° C., and then incubated with 100 mL rabbit polyclonal antibody against human neutrophil elastase (1:500 dilution) in the incubation buffer for 3 hours at 37° C. Following washing, a goat anti-rabbit IgG antibody conjugated with alkaline phosphatase (1:500 dilution) was added for 2 hours at 37° C. Finally, the plate was washed four times with the washing buffer and 100 substrate containing 1 mg/mL p-nitrophenyl-phosphate in 10 mM diethanolamine, 0.5 mM $MgCl_2$, pH 9.5 was added. Substrate hydrolysis was measured as described above.

The concentration of platelet factor 4 in the plasma after treatment of whole blood with various inflammatory mediators was determined by a competitive ELISA. Microplate wells were coated with 100 μL of purified platelet factor 4 at 0.5 mg/mL in PBS at 4° C. overnight. The plate was then washed twice with PBS and blocked with 2% BSA for 2 hours at 37° C. After another washing, a 100 μL incubation solution containing a constant concentration of platelet factor 4 antibody (2 mg/mL) and a diluted plasma sample (from 1:10 to 1:80 dilution) was added, and incubated at 37° C. for 4 hours. The plate was then washed with washing buffer. A goat anti-rabbit IgG antibody conjugated with alkaline phosphatase at a dilution of 1:500 in the incubation solution was then added for 2 hours at 37° C. Alkaline phosphatase activity was measured as described above.

For each ELISA plate, a standard curve was obtained by plotting the activity against concentration of purified protein used in each assay. Each sample was analyzed in duplicate by ELISA and average was calculated. The mean values of three separate experiments with standard deviation were reported.

aPTT Assays. Coagulation assays were performed in the microplate as described previously by Pratt and Monroe, 1992, *BioTechniques* 13:430. Briefly, 40 μL plasma (anticoagulated with sodium titrate) in each well was incubated with 40 μL buffer (20 mM HEPES, 150 mM NaCl and 0.1% polyethylene glycol, pH 7.4) containing the indicated reagents for 3 minutes at 25° C. 40 μL aPTT reagent was then added for 5 minutes at 25° C. Clotting was initiated by adding 40 μL of 25 mM $CaCl_2$. The clotting time was determined kinetically by time to Vmax at 405 nM as described by Lundblad, 1971, *Biochemistry* 10:2501. Relative clotting time (RCT) is calculated as the clotting time in the presence of 11 nM heparin divided by clotting time in the absence of added heparin for each individual plasma sample. No substantial differences in the aPTT were found for any of the plasma samples measured in the absence of heparin.

The plasmas obtained after treatment of whole blood with various agonists were prepared as follow: venous blood was collected in sodium citrate and 2 mL aliquots were mixed with various challengers at the indicated concentrations. The samples were incubated at 37° C. in a tissue culture incubator with 5% $CO_2$. At a specific time, the incubation was terminated by centrifugation at 2000 rpm for 10 minutes at 4° C. The plasma supernatant was collected and centrifuged again at 10,000 rpm for 5 minutes to remove contaminated platelets. Plasma samples thus obtained were used for both ELISA and aPTT assays.

For all the assays used in these studies, mean values and standard deviations (S.D.) were determined using Cricket Graph version III on a Macintosh IIsi computer.

Results

The heparin neutralization activity of lactoferrin in the antithrombin-thrombin inhibition reaction was compared to that of transferrin, platelet factor 4 and protamine sulfate. Various forms of lactoferrin, including milk lactoferrin, neutrophil lactoferrin, apolactoferrin and hololactoferrin, were also compared for this activity. Each reaction contained 0.1 µg/mL heparin (7 nM), 50 nM antithrombin, 5 nM thrombin and various concentrations of the indicated molecule. Residual thrombin activity was measured after 30 seconds incubation. Percentage of heparin neutralization is expressed by plotting extent of neutralization of anticoagulant activity against the molar ratio of neutralizing protein/heparin. The effect of a lactoferrin antibody (Lactoferrin-Ab) was analyzed by preincubation of the antibody (25 mg/mL) with lactoferrin for 30 minutes at room temperature before the addition of other reagents. Inclusion of 3 mM EDTA in the reaction did not affect heparin neutralization activity of lactoferrin. Preincubation of purified lactoferrin with a lactoferrin-polyclonal antibody significantly decreased lactoferrin activity.

Figure 2:
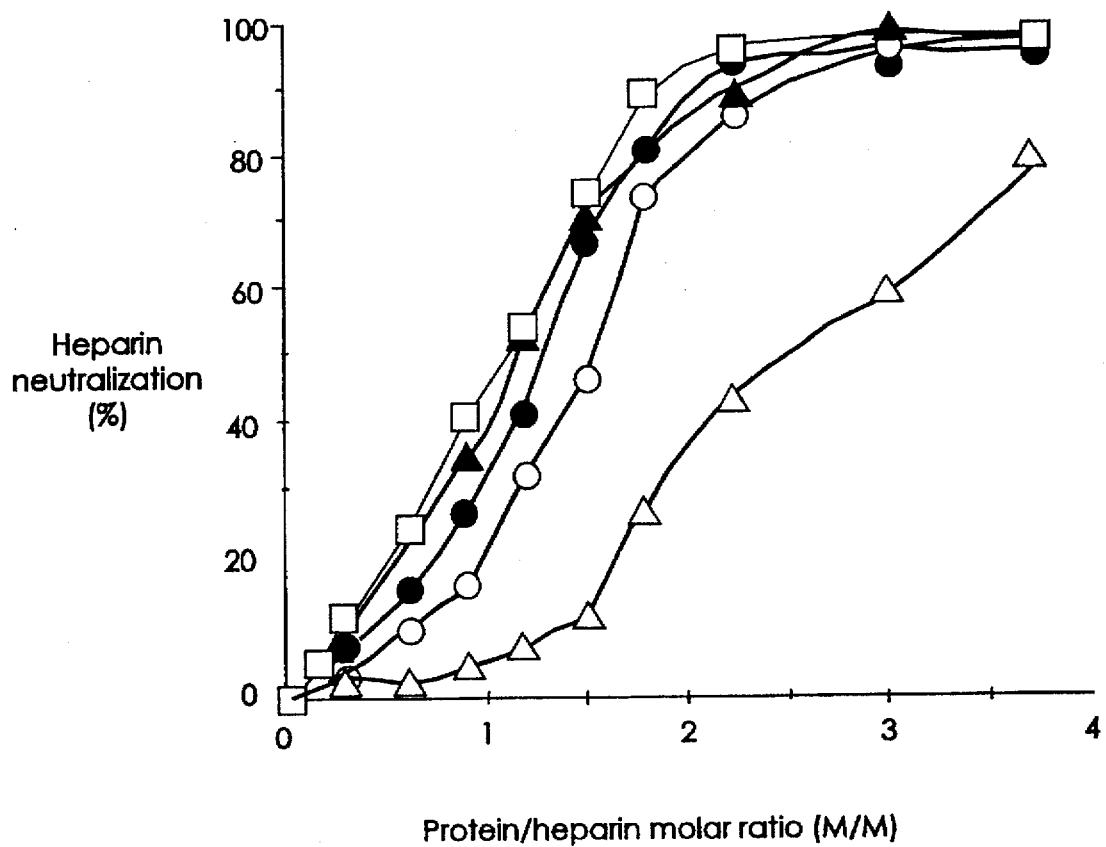

As shown in FIG. 1, lactoferrin obtained from either milk or neutrophils had heparin neutralization activity comparable to platelet factor 4, and they were both more effective than protamine sulfate. Transferrin did not have any heparin neutralization activity. As set forth in FIG. 2, similar results were obtained for heparin neutralization with the various forms of lactoferrin in the thrombin-heparin cofactor II inhibition reaction wherein each reaction contained 0.1 µg/mL heparin (7 nM), 50 nM heparin cofactor II, 5 nM thrombin and various concentration of indicated proteins. Residual thrombin activity was measured after 40 seconds incubation.

Figure 3A:
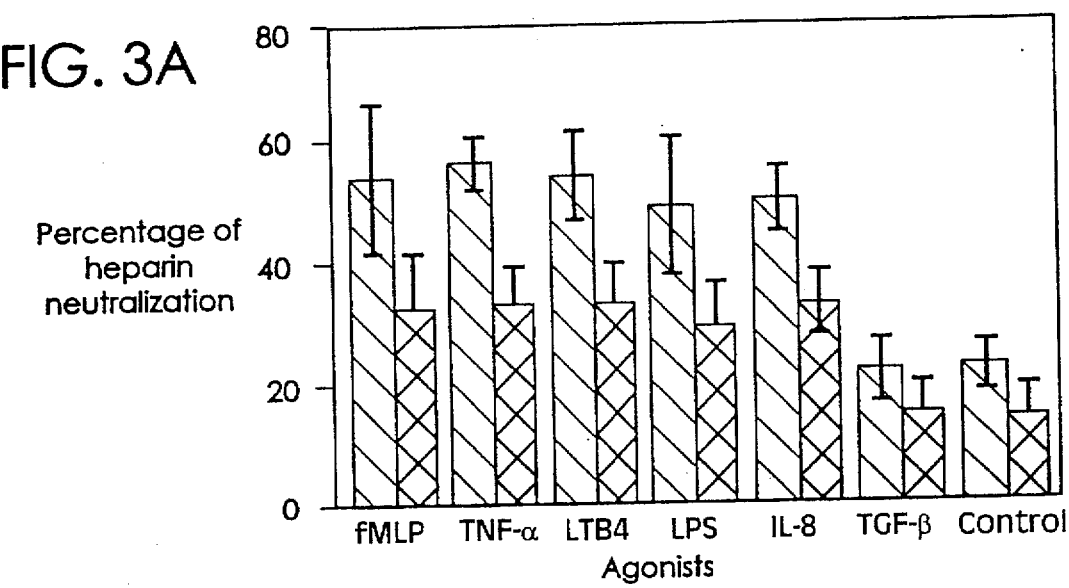

The ability of the products released by activated neutrophils to inhibit the heparin-catalyzed antithrombin-thrombin inhibition reaction was examined. Isolated neutrophils (107 cells/mL) were treated with 100 nM fMLP, 100 units/mL TNF-a, 100 nM LTB4, 1 mg/mL LPS, 500 nM IL-8 or 500 nM TGF-b for 30 minutes at 37° C. and the reactions were terminated by centrifugation. Each assay contained 23 ng/mL heparin (2 nM), 40 nM antithrombin, 20 mg/mL aprotinin, 200 mM TPCK and 40 mL of each neutrophil supernatant in a total volume of 130 mL. The reaction was initiated by adding 3 nM thrombin. Residual thrombin activity was measured after 90 seconds incubation and the percentage of heparin neutralization (p) calculated. For the antibody blocking assay, the neutrophil supernatants were pre-incubated with 25 mg/mL anti-lactoferrin polyclonal antibody, 20 mg/mL aprotinin and 200 mM TPCK for 30 minutes at room temperature before addition of other reagents (n). Results, as set forth in FIG. 3, are mean values (+S.D.) obtained from three separate experiments done in duplicate. The concentration of lactoferrin in these neutrophil supernatants was determined by ELISA. The results represent mean value (+S.D.) obtained from three separate experiments done in duplicate. The concentration of lactoferrin at 800 ng/mL is about 10 nM. The concentration of elastase in these neutrophil supernatants was measured by ELISA. The results represent mean value (+S.D.) obtained from three separate assays done in duplicate. As set forth in FIG. 3, the supernatants of neutrophils after challenge with fMLP, TNF-a, leukotriene B4 (LTB4), LPS, and interleukin-8 (IL-8) significantly neutralized the heparin activity in the thrombin-antithrombin reaction. However, treatment of neutrophils with the chemoattractant TGF-b did not have any effect compared to untreated neutrophils. Additionally, preincubation of the neutrophil supernatants with a polyclonal antibody against lactoferrin partly reduced the anti-heparin activity of neutrophil supernatants examined.

Figure 3B:
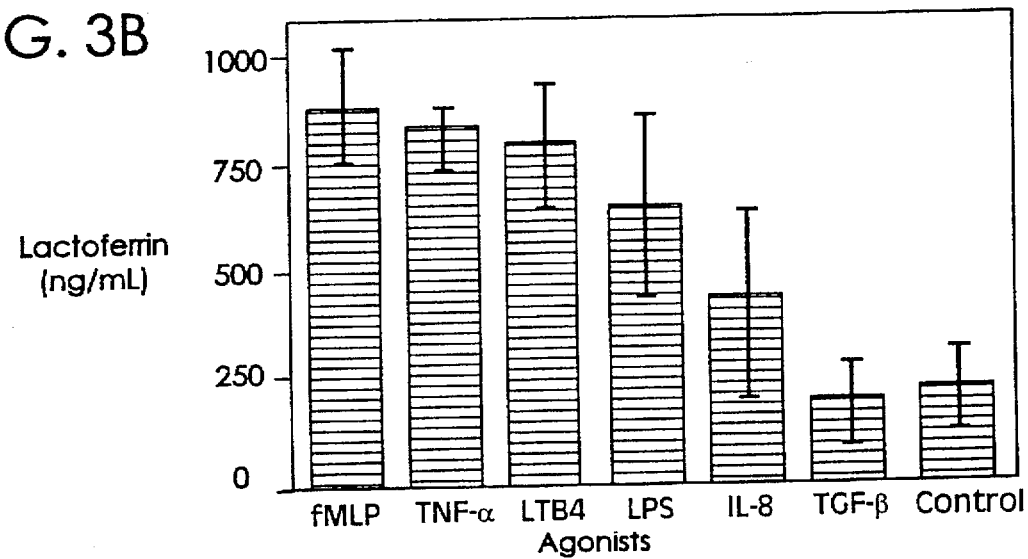
Figure 3C:
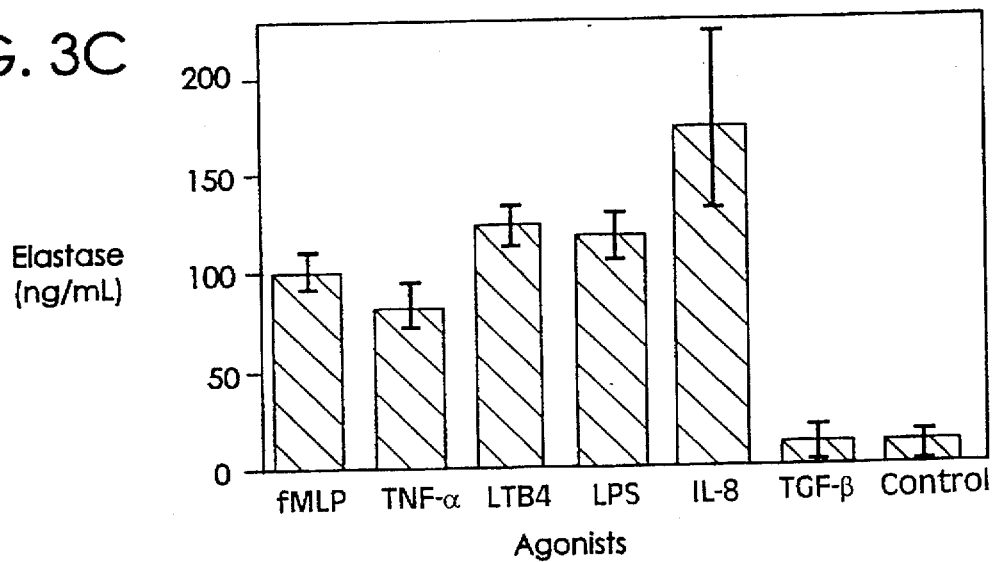

The concentration of both lactoferrin and the serine proteinase elastase in neutrophil supernatants was quantitated by ELISA. fMLP, TNF-α, LTB4, LPS, and IL-8 mediated significant release of lactoferrin from neutrophils (see, FIG. 3B). The mount of lactoferrin in these neutrophil supernatants was well correlated with the specific heparin neutralization activity (see, FIG. 3A). The concentration of elastase in these neutrophil supernatants was also increased significantly after the treatment with fMLP, TNF-a, LTB4, LPS, and IL-8 (see, FIG. 3C).

Figure 4:
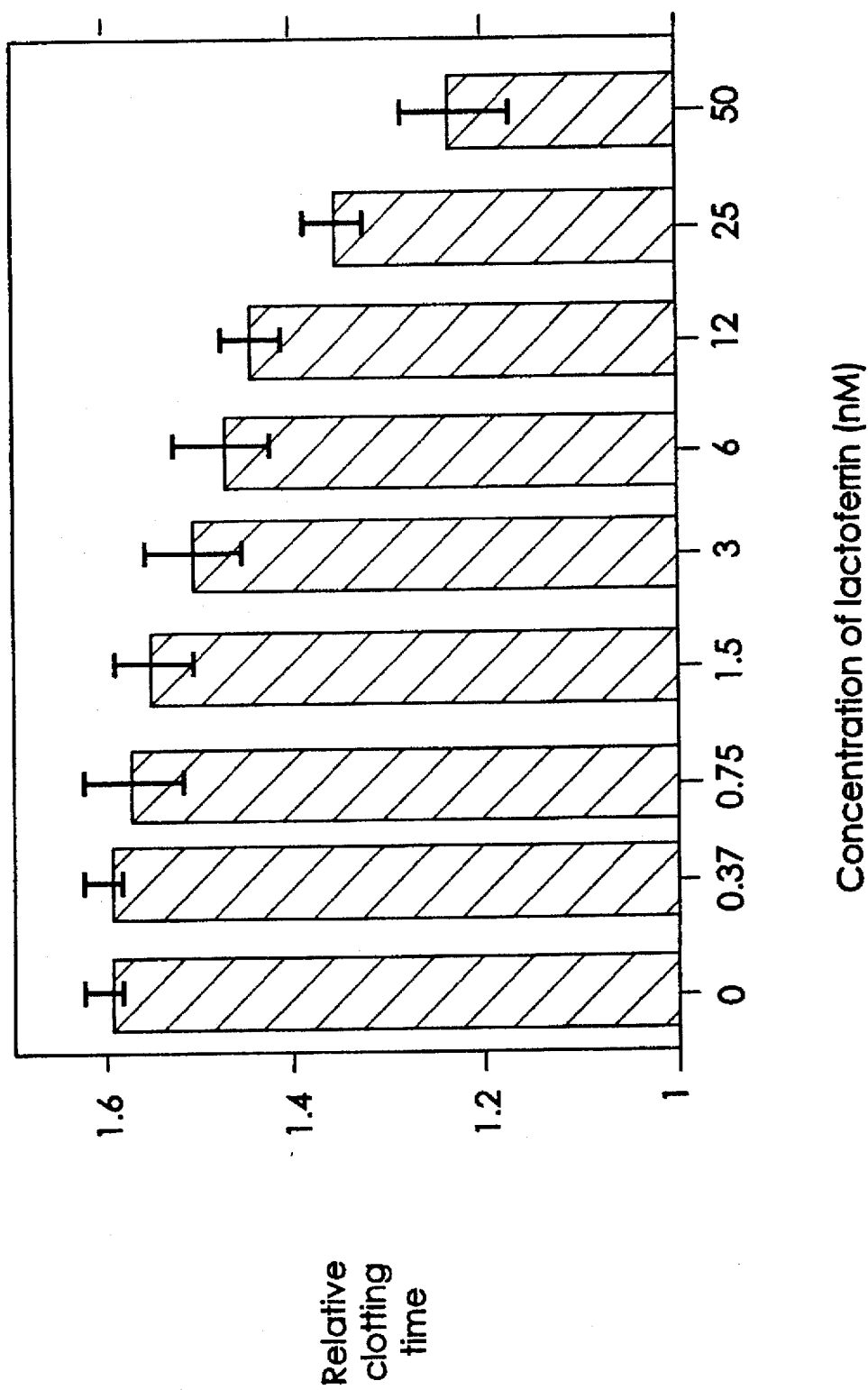

The ability of lactoferrin to neutralize heparin in the complex system of blood plasma coagulation was investigated. Normal pooled plasma was used in this assay. Each reaction contained 11 nM (0.166 mg/mL) heparin and the various concentrations of lactoferrin as indicated. Results are the mean values (+S.D.) obtained from three separate experiments performed in duplicate. As set forth in the data presented at FIG. 4, prolongation of the aPTT in heparinized plasma was expressed as the ratio of the aPTT in the presence of heparin to the aPTT in the absence of heparin (RCT; relative clotting time). In heparinized plasma, the RCT was reduced by addition of lactoferrin in a dose-responsive manner.

Figure 5A:
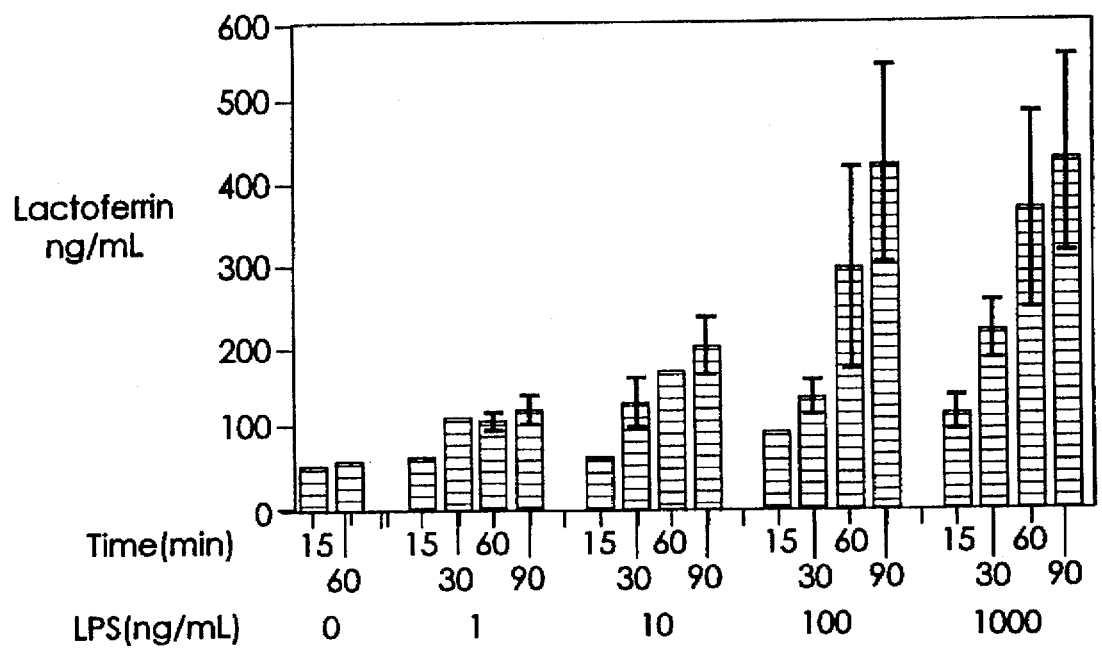
Figure 5B:
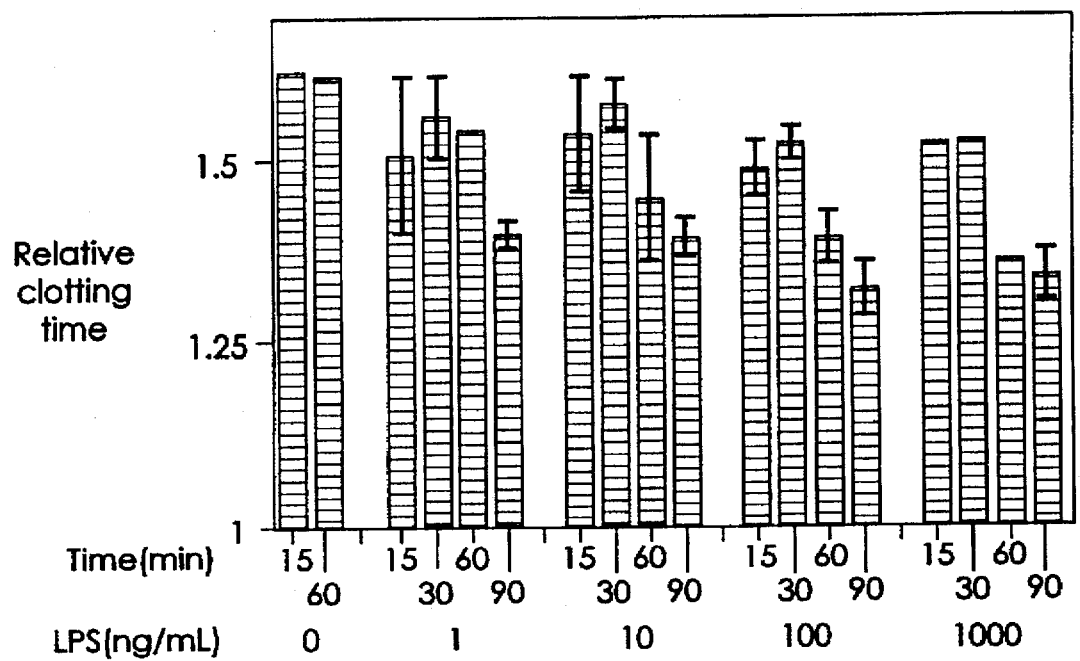

The concentration of plasma lactoferrin was also determined by ELISA after incubation of whole blood with LPS. LPS from *Salmonella minnesota* was obtained from Sigma. Whole blood (2 mL) freshly obtained was incubated with LPS for the indicated time period and at the various concentrations listed. The reactions were terminated by centrifugation. The concentration of plasma lactoferrin was determined by ELISA. For each LPS-treated blood sample, RCT represent aPTT ratio of heparinized plasma to unheparinized plasma. Results are reported as the mean value (+S.D.) obtained from three separate experiments performed in duplicate. As shown in FIG. 5, the plasma lactoferrin concentration increased in response to LPS treatment in a time- and dose-dependent manner. Prolongation of the aPTT by adding heparin to plasma was reduced in LPS-treated blood.

Figure 6A:
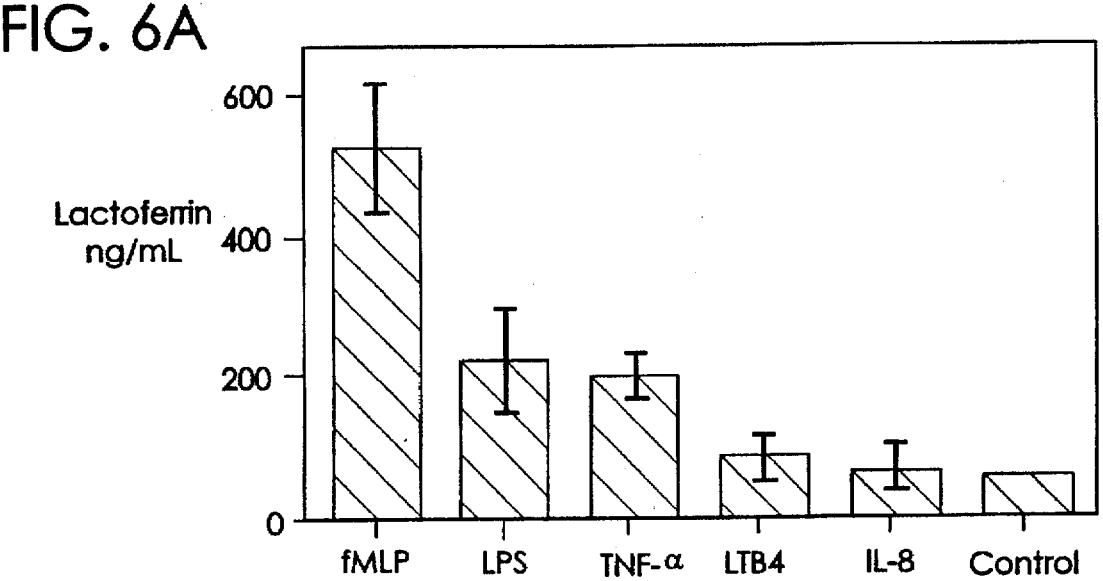
Figure 6B:
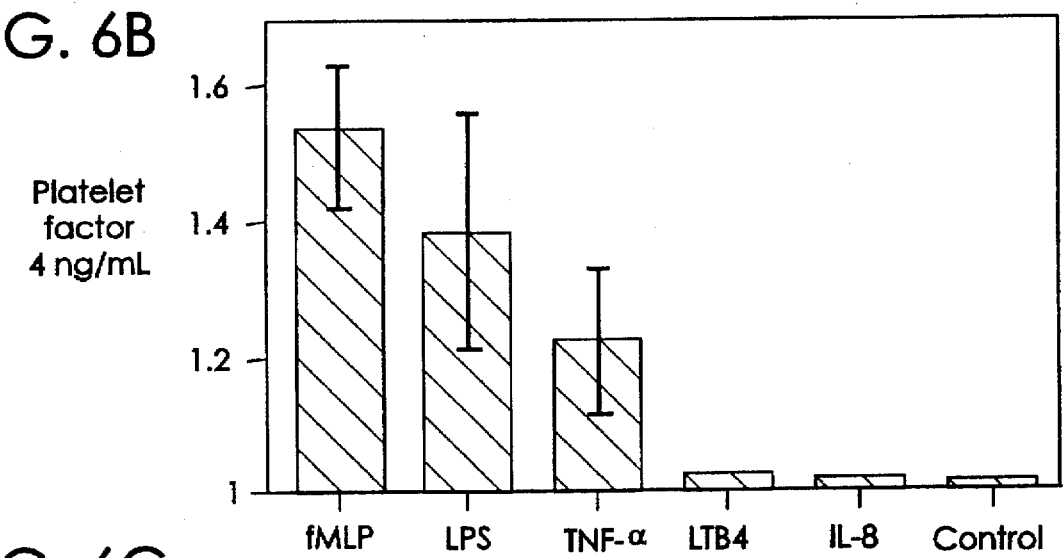
Figure 6C:
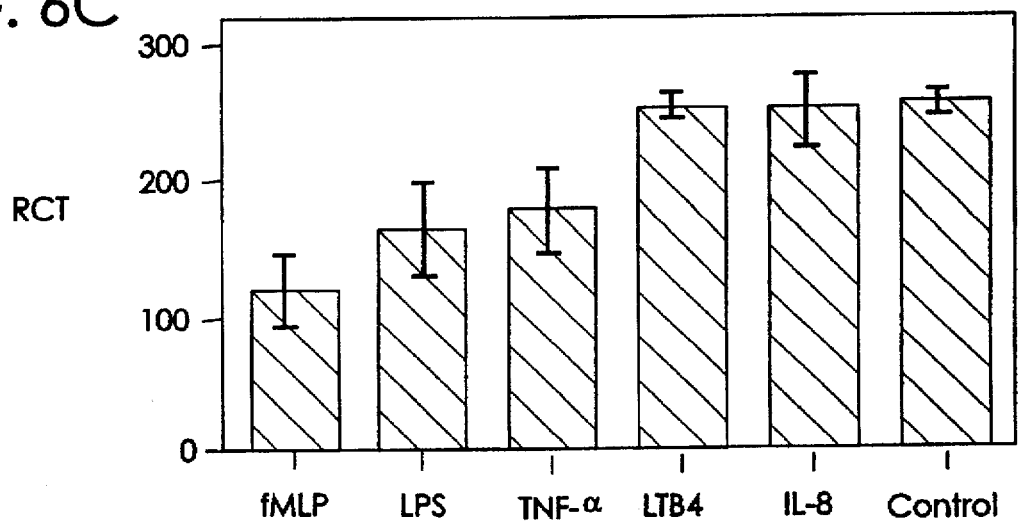

The plasma concentration of both lactoferrin and platelet factor 4 after treatment of whole blood with the various agonists was then quantitated by ELISA. Whole blood which was anticoagulated with sodium citrate was treated with various agonists (at the same concentrations as described in FIG. 3) for 30 minutes at 37° C. The concentration of lactoferrin and platelet factor 4 were measured by ELISA in the plasma obtained from each agonist-treated blood sample and an aPTT was performed to determine RCT. The mean value (+S.D.) of three separate experiments done is duplicate is reported for all assays. Control experiments showed that all the inflammatory mediators did not alter RCT values when incubated with pooled human plasma. The treatment of blood with fMLP, LPS and TNF-a resulted in a significant increase in both lactoferrin and platelet factor 4 levels while other neutrophil agonists such as IL-8, LTB4 did not have any effect to increase plasma levels of either protein. As set forth in FIG. 6, examination of the RCT of plasma obtained from these treated blood samples showed a reduction of RCT for the blood treated with LPS, fMLP, TNF-α.

EXAMPLE

Characterization Of Lactoferrin Activity To Neutralize Three Known Glycosaminoglycans During Thrombin Inhibition Materials And Methods Materials. Chromogenic substrate (tosyl-Gly-Pro-Arg-p-nitroanilide) for the measurement of thrombin activity and *Staphylococcus aureas* $V_8$ protease were obtained from Boehringer-Mannheim. Polybrene, heparin and heparin sulfate were obtained from Aldrich Chemical Co., Diosynth (Oss, the Netherlands), and Enzyme Research Lab, Inc., respectively. Applicants obtained dermatran sulfate from CalBioChem. Human lactoferrin was purified from fresh milk using the techniques described in Blackberg and Hemell, 1980, *FEBS Lett*. Human α-thrombin, antithrombin and heparin cofactor II were purified according to the procedures described in Lundblad, 1971, *Biochemistry* 10:2501–2506 and Griffth, et al., 1985, *J. Biol. Chem.* 260:2218–2225.

Thrombin-Serpin Reactions. The assay was performed in 96-well U-bottom microplates (Becton-Dickinson) in 100 μl of 0.15M NaCl, 0.02M Hepes, 1 mg/ml polyethylene glycol ($M_r$ 8000) and 1 mg/ml bovine serum albumin (pH 7.4).

To determine thrombin inhibition rate, the reaction mixtures contained 50 nM serpin, various concentrations of glycosaminoglycan, and a constant concentration of lactoferrin (0.1 μM lactoferrin for heparin-, 0.2 μM for heparan sulfate-, or 0.5 μM for dermatran sulfate-catalyzed reactions). The reaction was initiated by adding thrombin (5 nM) to the microplate well. After an incubation of 5 to 30 seconds, 50 μl of a solution containing 0.2 mM tosyl-Gly-Pro-Arg-p-nitroanilide and 3 mg/ml Polybrene was added. Residual thrombin activity was determined by measuring the hydrolysis of the chromogenic substrate in a Molecular Devices Vmax kinetic microplate reader. Second-order inhibition rate constants were calculated as $-[\ln(\alpha)/t \times [I]]$, where α is the fractional thrombin activity remaining relative to the uninhibited control, t is the time for incubation, and [I] is the serpin concentration. Each experiment was conducted at least three times and data is presented in mean values.

For the determination of kinetic parameters for thrombin-serpin reaction, the initial reaction velocity ($V_i$) was calculated according to the general equation for a random-order bioreactant enzyme catalyzed reaction disclosed in Griffith, 1982 *J. Biol. Chem.* 257:7360–7365; Griffith, 1983, *Proc. Natl. Acad. Sci.* 80:5460–5465; Speight and Griffith, 1983, *Arch. Biochem. Biophys.*, 225:958–963. 0.33 nM of heparin and 187 nM lactoferrin were included in the assays, The reaction contained a constant concentration of thrombin (5 nM) while varying that antithrombin (50 to 300 nM) or a constant concentration of antithrombin (200 nM) while varying the concentration of thrombin (2.5 to 20 nM). The assays were staffed by addition of thrombin of to the reaction wells. After an incubation of period of about 60 seconds, 50 μl of a solution containing 0.3 mM tosyl-Gly-Pro-Arg-p-nitroanilide and 1.5 mg/ml Polybrene was added to measure the residual thrombin activity. The data presented are mean values of duplicate assays performed two times.

Purification of lactoferrin peptides. 50 mg of purified milk lactoferrin was dialyzed against 0.1M sodium acetate (pH 4.0) for three hours at room temperature and incubated with 0.5 mg $V_8$ protease for 20 hours at 37° C. Purification of lactoferrin peptides was performed at room temperature. The lactoferrin-$V_8$ digest was loaded onto a heparin-Sepharose column (1.5×10 cm) which was equilibrated with 20 mM Hepes containing 200 mM NaCl (pH 7.4). The bound proteins were eluted by a linear salt gradient (200 to 1000 mM NaCl) in 20 mM Hepes (pH 7.4). The protein peak with the highest affinity to heparin-Sepharose was collected and further fractionated by size-exclusion chromatography on a G-75 Sephadex (3×40 cm) to remove high-molecular weight contaminants. The purified lactoferrin peptides were further separated using a $C_4$ column and reversed-phase chromatography prior to automated amino-terminal sequencing using an ABI Model 475A sequencer.

Glyoscaminoglycan neutralization assay. The assay was performed in 96-well U bottom microplates in 100 μl of the buffer described above. The reaction contains 50 nM serpin, various concentrations of lactoferrin or lactoferrin peptides and a constant concentration of glycosaminoglycan (0.1 μg/ml heparin, 2.3 μg/ml heparan sulfate or 1 μug/ml dermatan sulfate). The reaction was initiated by adding thrombin (5 nM) to the microplate well. After incubation for 30 seconds, 50 μl of a solution containing 0.2 mM tosyl-Gly-Pro-Arg-p-nitroanilide and 1.5 mg/ml Polybrene was added and the residual thrombin activity was determined. All neutralization assays were performed at least three times and mean values were determined. Percentage of glycosaminoglycan neutralization is expressed by plotting extent of neutralization of the thrombin-serpin reaction against the molar ratio of either lactoferrin or lactoferrin peptides to glycosaminoglycan in the reaction. The molarity of each glycosaminoglycan was calculated based on a dry weight basis using $M_r$'s of 15, 30 and 50 kDa for heparin, heparan sulfate and dermatan sulfate, respectively. Percentage of glycosaminoglycan neutralization was calculated as: percentage of glycosaminoglycan neutralization=[(B−A)/(C−A)]×100%, where A is the residual thrombin activity obtained in the presence of serpin and glycosaminoglycan; B is the activity obtained in the presence of serpin, glycosaminoglycan and lactoferrin or lactoferrin peptides; and C is the activity obtained in the presence of serpin only. The control experiments verified that lactoferrin or lactoferrin peptides did not alter: (1) the activity of thrombin alone, (ii) the activity of thrombin in the presence of glycosaminoglycan, (iii) the thrombin inhibition by the serpins in the absence of glycosaminoglycan.

Protein Binding To Heparin-Sepharose. Experiments were performed at room temperature using a Pharmacia FPLC system. A FPLC heparin-Sepharose column (~1-ml bed volume) was used for analysis of the heparin binding proteins. A 100 μl sample containing either protein or peptide (~100 μg/ml) in 20 mM Hepes containing 50 mM NaCl (pH 7.4) at a flow rate of 2 ml/min. The relative binding affinity of each protein or peptides for heparin-Sepharose was estimated based on the concentration of salt needed to elute protein from the column as described previously in Pratt and Church, 1992, *J. Biol. Chem.* 267:8789–8794. The means and standard deviations were calculated from multiple (three to five) runs.

Results

Figure 7A:
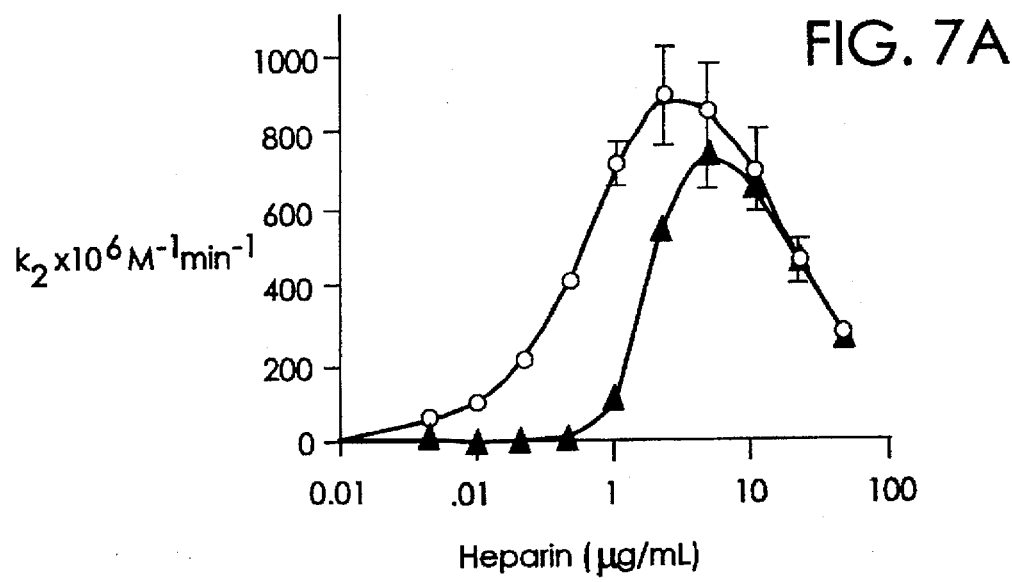
Figure 7B:
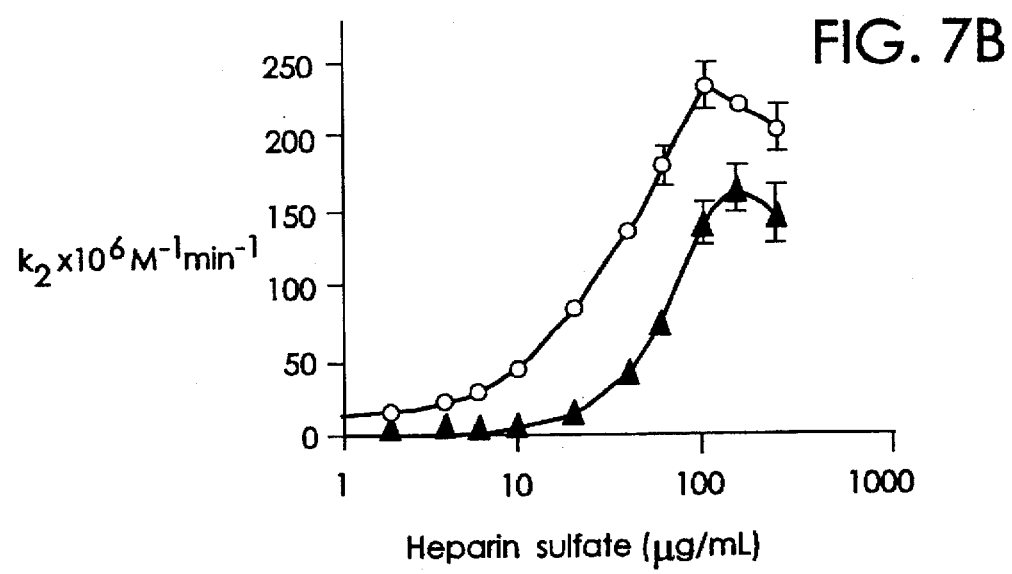
Figure 7C:
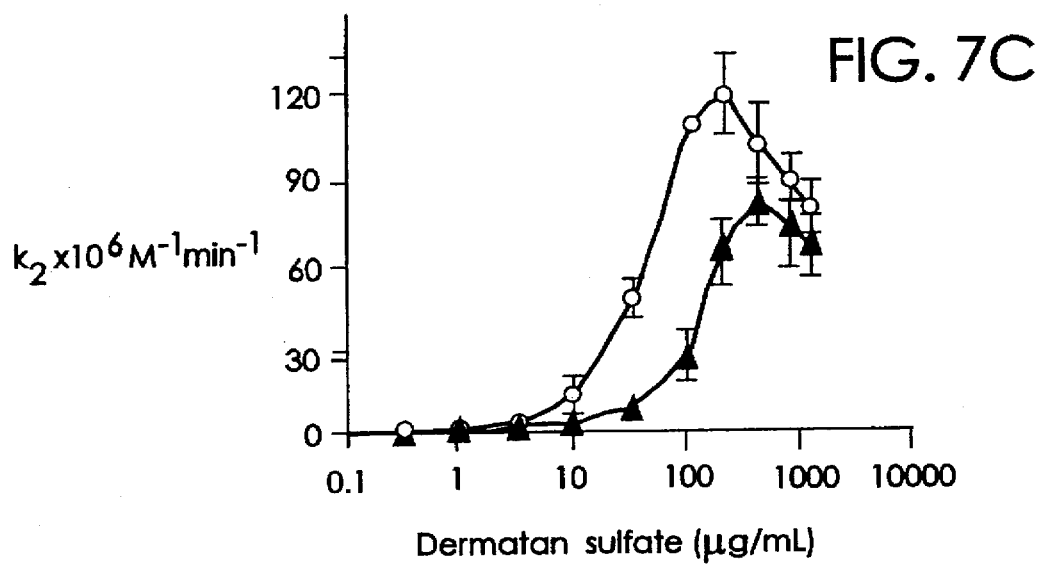

The ability of lactoferrin to inhibit heparin-, heparan sulfate- and dermatan sulfate-catalyzed serpin-thrombin inhibition reaction was examined. Since each glycosaminoglycan has a different optimal concentration for the maximal inhibition rate, a different concentration of lactoferrin (0.1 to 0.5 μM) was chosen in each reaction. Antithrombin was used for the heparin- and heparan sulfate-catalyzed reactions, while heparin co-factor II was used with dermatan sulfate. As shown in FIG. 7, the inclusion of lactoferrin reduced the maximum rate of thrombin inhibition catalyzed by all three glycosaminoglycans. The optimal glycosaminoglycan concentration for each reaction was shifted to a higher concentration by the addition of lactoferrin.

Figure 8A:
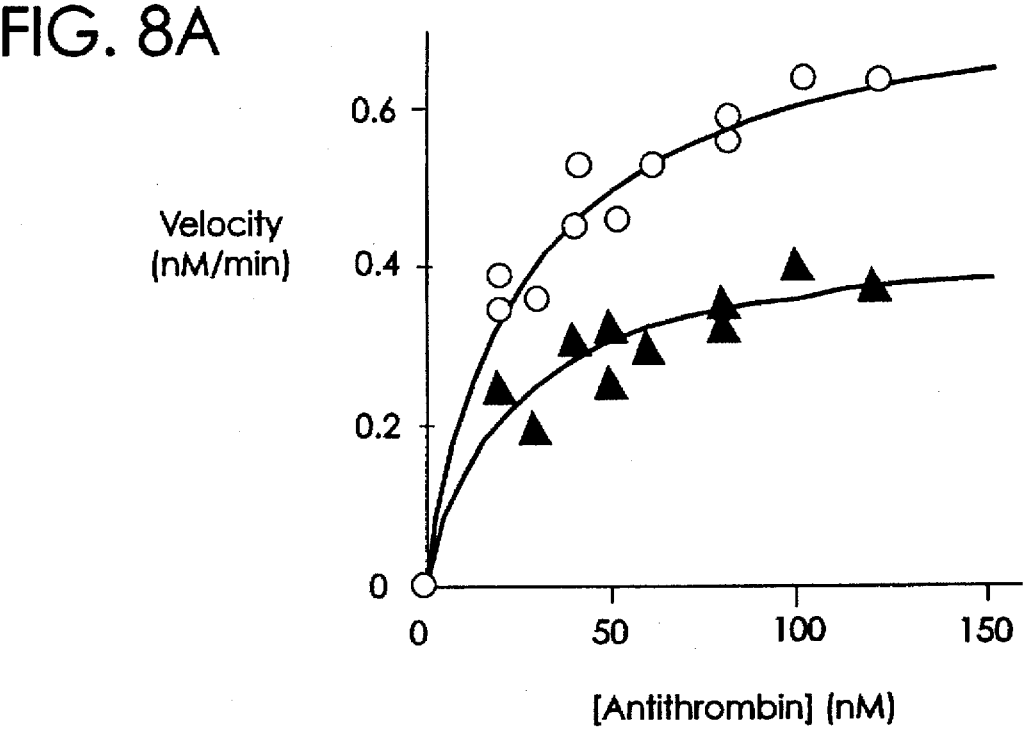
Figure 8B:
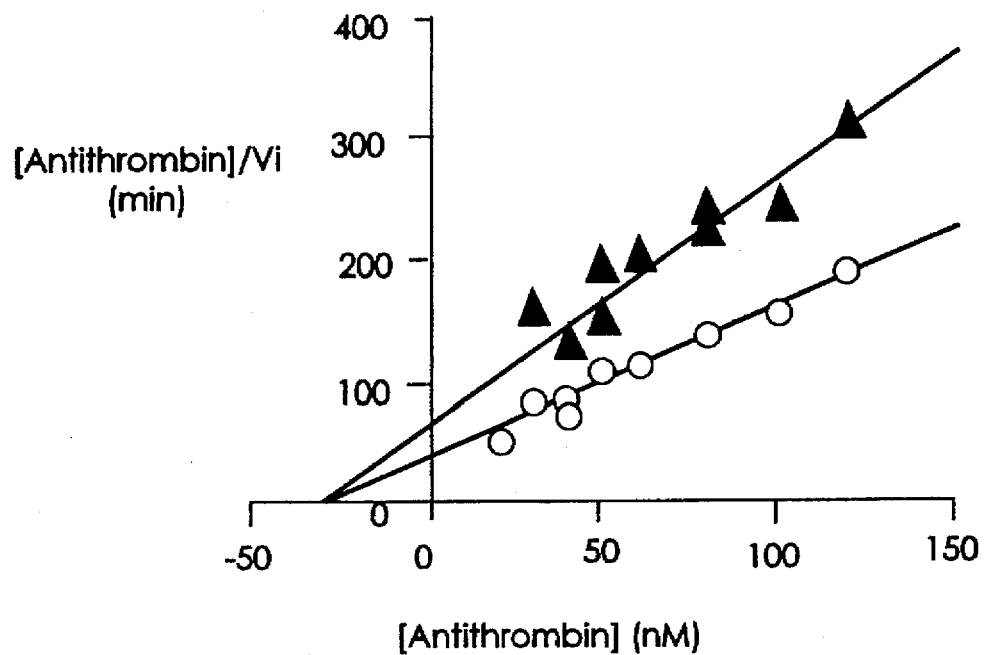

Effect Of Lactoferrin On The Kinetic Parameters For The Heparin-Catalyzed Thrombin-AntiThrombin Reaction. The data for thrombin inhibition as a function of the concentration of antithrombin are plotted in FIG. 8. The initial rate of thrombin inhibition by antithrombin in the presence of heparin (0.33 nM) was determined in the presence and absence of lactoferrin (0.187 nM), as described above. In FIG. 8A, the initial thrombin inhibition velocity was plotted as a function of the concentration of antithrombin. The thrombin concentration in the reaction was 2 nM. FIG. 8B reflects the same data plotted as [S]/V vs. [S] wherein (○) indicates control and (△) indicates lactoferrin.

All of the kinetic parameters for the heparin-catalyzed thrombin-antithrombin reactions are summarized at Table 1.

TABLE 1

Effect Of Lactoferrin On The Apparent Kinetic Parameters For The Heparin-Catalyzed Thrombin-Antithrombin Reactions

| | $K_{AT}$ (nM) | $V^{AT}_{max}$ (nM/min) | $K_T$ (nM) | $V^T_{max}$ (nM/min) |
|---|---|---|---|---|
| Control | 27.5 ± 5.2 | 0.76 ± 0.05 | 8.6 ± 1.4 | 3.49 ± 0.25 |
| Lactoferrin | 25.1 ± 7.8 | 0.45 ± 0.05 | 8.2 ± 2.2 | 2.30 ± 0.27 |

Lactoferrin did not have a measurable effect on the apparent dissociation constant but it did decrease the apparent maximum reaction velocity at saturation with respect to both antithrombin and thrombin. These data suggested that lactoferrin was a noncompetitive inhibitor and effectively destroy heparin's activity. This conclusion was further supported by an additional experiment which showed that none of the heparin activity could be recovered by adding a large excess of both thrombin and antithrombin when the concentration of lactoferrin (2 nM) was 2.5-fold higher than heparin (0.66 nM) in the reaction.

Figure 9A:
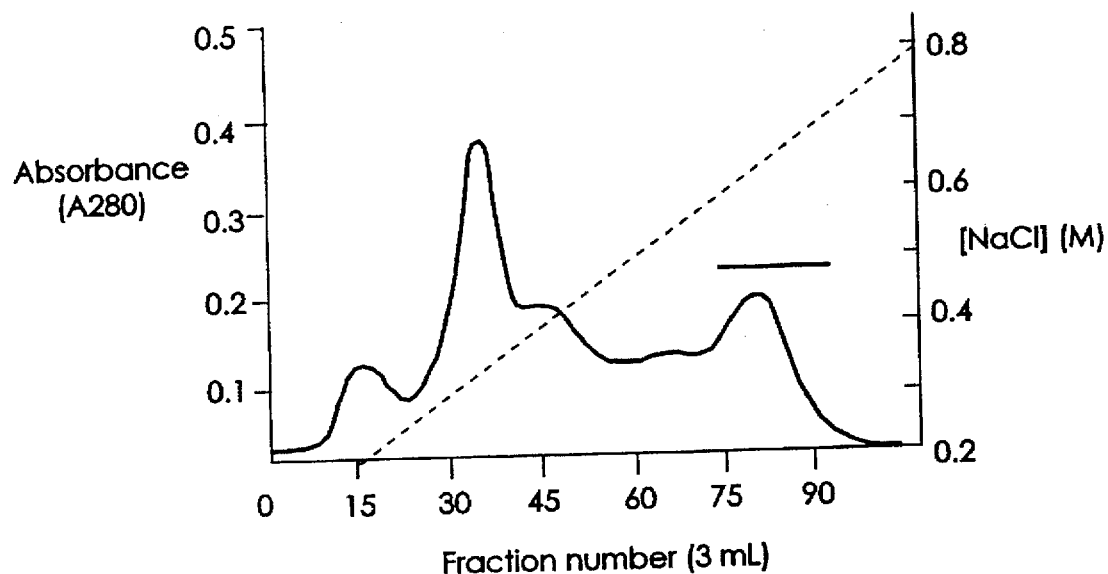
Figure 9B:
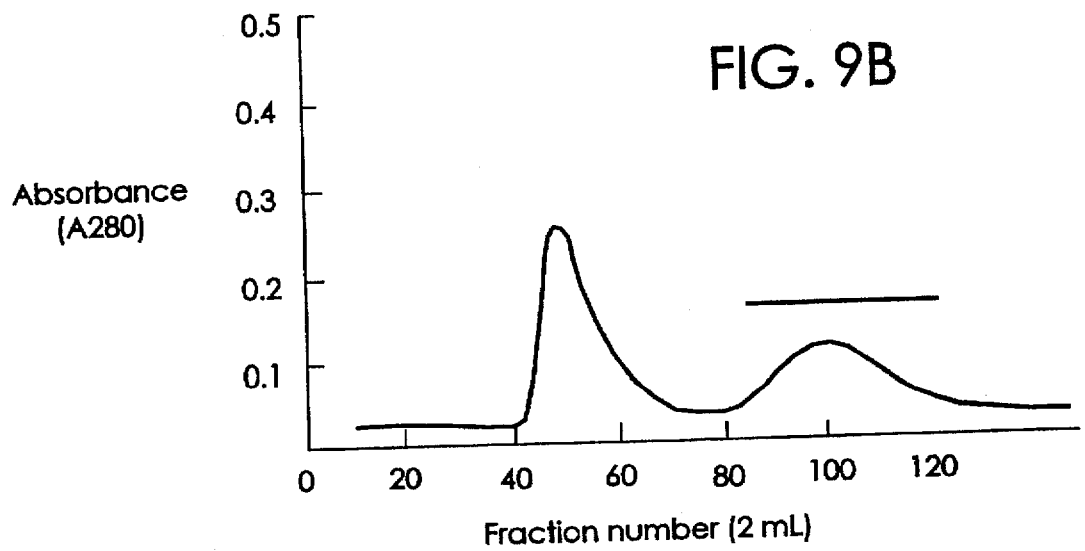

Isolation Of Heparin-Binding Peptides From Lactoferrin. Heparin-binding peptides derived from lactoferrin after limited proteolysis with $V_8$ protease were obtained by heparin-Sepharose chromatography (FIG. 9A). The proteins which were eluted at the highest salt concentration were collected and analyzed by SDS-PAGE on a 8 to 27% gradient gel. This fraction was composed of both low-molecular-weight proteins with M/s of 8 and 11 kDa and other proteins at about 80 to 40 kDa. The higher Mr contaminants (about 80 and 40 kDa) were most likely undigested intact lactoferrin and the N-terminal half of lactoferrin, respectively. Therefore, gel filtration using G-75 Sephadex was used to remove the higher Mr contaminants (FIG. 9B). Two lactoferrin peptides with essentially the same affinity to heparin-Sepharose were purified and characterized by SDS-PAGE. Specifically, the purified lactoferrin peptides were analyzed in a 8–27% nonreducing polyacrylamide gel. Myosin (200 kDa), galactosidase (116 kDa), phosphorylase b (97 kDa), bovine serum albumin (66 kDa), glutamic dehydrogenase (55 kDa), lactate dehydrogenase (36 kDa), carbonic anhydrase (31 kDa), soybean trypsin inhibitor ((21.5 kDa), lysozyme (14.4 kDa) and aprotinin (6 kDa) were used as molecular weight markers. The two purified lactoferrin peptides have an approximate weight of 8 kDa and 10.5 kDa, as measured against these markers.

Figure 10A:
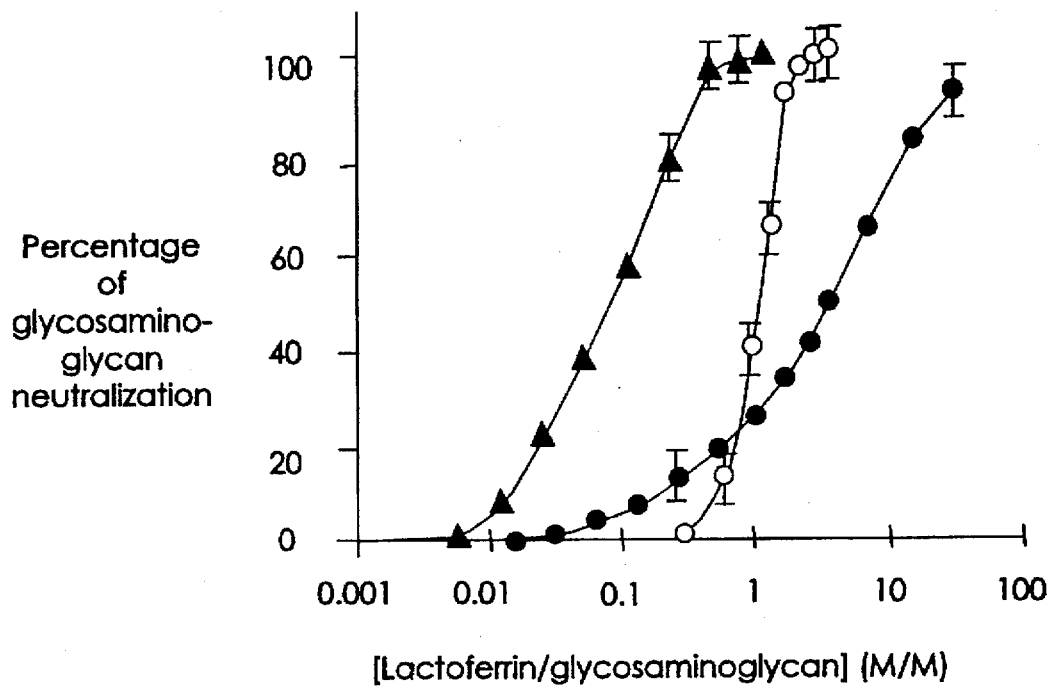
Figure 10B:
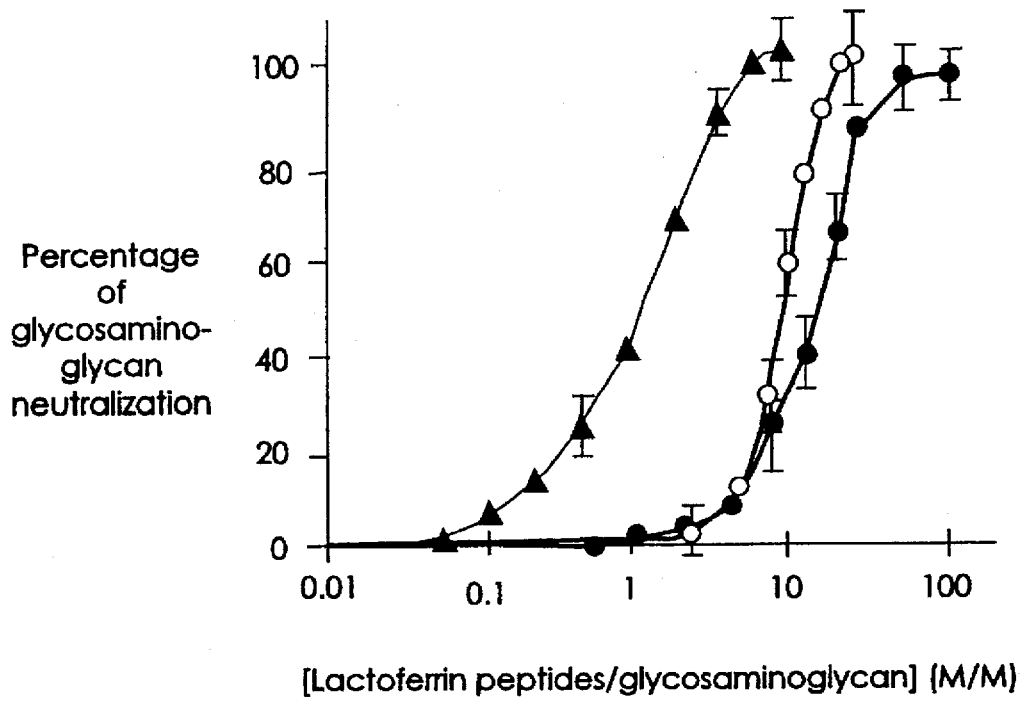

Characterization Of N-Terminal Lactoferrin Peptides. The lactoferrin peptides described above were separated on a $C_4$ matrix and subjected to amino acid sequence analysis for 17 cycles. The sequence analysis revealed that both peptides derived from the N-terminus of lactoferrin. Since the $V_8$ protease specifically hydrolyzes on the carboxyl side of the Glu residue at pH 4.0, the 8 kDa peptide likely ends at $Glu^{67}$, while the 10.5–11 kDa peptide terminates at either $Glu^{81}$ or $Glu^{86}$. Because both lactoferrin peptides were from the N-terminus and were copurified under the same elution conditions following heparin-Sepharose and G-75 Sephadex chromatographies, they were used for subsequent assay without farther separation. The ability of the lactoferrin peptides, compared to the intact lactoferrin molecule, to neutralize glycosaminoglycan-catalyzed thrombin-serpin reactions was determined according to the method described above. The results are set forth at FIG. 10.

The relative affinities of both lactoferrin and lactoferrin peptides to heparin were also analyzed based on the concentration of salt required to elute protein from heparin-Sepharose. The results were compared to other heparin-binding proteins. As set forth in Table 2, both intact lactoferrin (770 mM) and the lactoferrin peptides (685 mM) were eluted from heparin-Sepharose at higher salt concentrations than that for thrombin and heparin cofactor II but at lower salt concentrations than that for antithrombin.

TABLE 2

Heparin affinity of Lactoferrin And Lactoferrin Peptides

| Protein | Relative heparin affinity [NaCl] (mM) |
|---|---|
| Lactoferrin | 770 ± 8 |
| Lactoferrin peptides | 685 ± 7 |
| Thrombin | 610 ± 4 |
| Antithrombin | 1010 ± 12 |
| Heparin cofactor II | 395 ± 9 |

The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited within the body of the instant specification are hereby incorporated by reference in their entirety. In addition, the publications listed below are of interest in connection with various aspects of the invention and are incorporated herein as part of the disclosure:

Roberts and Lozier, 1992, Hosp. Pract. 97;

Furie and Furie, 1992, N. Engl. J. Med. 326:800;

Broze, G J, Jr., Girard, T J, Novomy, W F, 1990, Biochemistry 29:7539;

Esmon, C T, 1992, Arterioscl. Thromb. 12:135;

Olson, S T, Björk, I., "Regulation of thrombin by antithrombin and heparin cofactor II." Thrombin: Structure and Function. Berliner ed. 1992 Plenum Press. New York, N.Y.

Pratt, C W, Church, F C, 1991, Sero. Hematol. 28:3;

Rosenberg, R D, Armand, G, Lain, L, 1978, Proc. Natl. Acad. Sci. USA 75:3065;

Sadler, J E, Lentz, S R, Sheehan, J P, Tsiang, M, Wu, Q, 1993, Haemostasis 23(suppl): 183;

Rosenberg, R D, Damus, P S, 1973, J. Biol. Chem. 248:6490;

Pratt, C W, Church, F C, 1993, Blood Coag. Fibrinol. 4:479;

Bick, R Lm 1988, Sem. Thromb. Hemosta. 14:299;

Bick, R L, Ucar, K, 1992, Hematol. Oncol. Clin. North. Am. 6:1421;

Larcan, A, Lambert, H, Gerard, A. "Consumption of coagulopathy." 1987 Marson. New York USA;

Spero, J, Lewis, J, Hasiba, 1980, Thrombo. Haemost. 42:28;

Iyer, S, Lonnerdal, B, 1993, Eur. J. Clin. Nutr. 47:232;

Masson, P L, Heremarts, J F, Schonne, E, 1969, J. Exp. Med. 130:643;

Lash, J A, Coates, T D, Lafuse, J, Baehner, R L, Boxer, La., 1983, Blood 61:885;

Adeyemi, E O, Campos, L B, Loizou, S, Walport, M J, Hodgson, H J, 1990, Br. J. Rheumatol. 29:15;

Adeyemi, E O, DAnastasio, C, Impallomeni, M G, Hodgson, H J, 1992, Aging Milano 4: 135;

Nuijens, J H, Abbink, J J, Wachtfogel, Y T, Colman, R W, Eerenberg, A J, Dors, D, Kamp, A J, Strack, v S R J, Thijs, L G, Hack, C E, 1992, J. Lab. Clin. Med. 119:159;

Koivuranta-Vaara, P, Banda, D, Goldstein, I M, 1987, Infect. Immun. 55:2956;

Palma, C, Cassone, A, Serbousek, D, Pearson, C A, Djeu, J Y, 1992, Infect. Immun. 60:4604;

Blackberg, L, Hemell, O, 1980, FEBS Letters 109:180;

Zou, S, Magura, C E, Hurley, W L, 1992, Comp. Biochem. Physiol. [b]103:889;

Metz-Boutigue, M, Jolles, J, Mazurier, I, Schoentgen, F, Legrand, D, Spik, G, Montreuil, I, Jolles, P, 1984, Eur. J. Biochem. 145:659;

Anderson, B F, Baker, H M, Norris, G E, Rice, D W, Baker, E N, 1989, J. Mol. Biol. 209:711;

Powell, M J, Ogden, J E, 1990, Nucleic Acids Res. 18:4013;

Anderson, B F, Baker, H M, Norris, G E, Rumball, S V, Baker, E N, 1990, Nature 344:784;

Mann, D M, Holland, J H, 1994, FASEB Journal 8:Abstract #5176;

Lundblad, R L, 1971, Biochemistry 10:2501;

Griffith, M J, Noyes, C M, Church, F C, 1985, J. Biol. Chem. 260:2218;

Kalmar, J R, Arnold, R R, Warbington, M L, Gardner, M K, 1988, J. Immunol. Meth. 110:275;

Lassiter, M O, Newsome, A L, Sams, L D, Arnold, R R, 1987, J. Dent. Res. 66:480;

Pratt, C W, Monroe, D M, 1992, BioTechniques 13:430;

de Agostini, A I, Watkins, S C, Slayter, H S, Youssoufian, H, Rosenberg, R D,1990, J. Cell Biol. 111:1293;

Marcum, J A, Rosenberg, R D, 1987, Sem. Thromb. Hemost. 13:464;

Mertens, G, Cassiman, J J, Van den Berghe, H, Vermylen, J, David, G, 1992, J. Biol. Chem. 267:20435;

McGuire, E A, Tollefsen, D M, 1987, J. Biol. Chem. 262:169;

van Deerlin, V M D, Tollefsen, D M, 1991, J. Biol. Chem. 266:20223;

Whinna, H C, Choi, H U, Rosenberg, L C, Church, F C, 1993, J. Biol. Chem. 268:3920;

Johnson, D, Travis, J, 1979, J. Biol. Chem. 254:4022;

Carp, H, Janoff, A, 1983, Adv. Inflam. Res. 5:173;

Tollefsen, D M, Pestka, C A, 1985, J. Clin. Invest. 75:496;

Loscalzo, J, Melnick, B, Hardin, R I, 1985, Arch. Biochem. Biophys. 240:446;

Saba, H L, Roberts, H R, Herion, J C, 1968, Blood 31:369;

Herion, J C, Bucher, J R, Penniall, R, Walker, R I, Baker, M, Roberts, H R, 1979, Am. J. Hematol. 7:265;

Day, C L, Stowell, K M, Baker, E N, Tweedie, J W, 1992, J. Biol. Chem. 267: 13857;

Day, C L, Anderson, B F, Tweedie, J W, Baker, E N, 1993, J. Mol. Biol. 232: 1084;

Lane, D A, Pejler, G, Flynn, A M, Thompson, E A, Lindahi, U, 1986, J. Biol. Chem. 261:3280;

Niwa, M, Yamagishi, R, Kondo, S, Sakuragawa, N, Koide, T, 1985, Thromb. Res. 37:237;

Horn, R G, Collin, R D, 1968, Lab. Invest. 18:101;

MacKay, D G, Shapiro, S S, 1958, J. Exp. Med. 107:353;

Parker, R I, McKeown, L P, Gallin, J I, Gralnick, H R, 1992, Thromb. Haemost. 67:320;

Hotrow, J. C., 1985, Anesth. Analg. 64: 348–361;

Just-Viera, J. O.,C. R. Fisher, O. Gago, and D. J. Morris, 1985, Am. Surg. 50: 52–60;

Maione, T. E., G. S. Gray, I. Peter, A. J. Hunt, A. L. Donner, S. I. Bauer, H. F. Carson, and R. I. Sharpe, 1990, Science 247: 77–79;

Maione, T. E., G. S. Gray, A. I. Hunt, and R. J. Sharpe, 1991, Cancer Res. 51: 2077–2083;

Slungaard, A., and N. S. Key, 1994, J. Biol. Chem. 269: 25549–25556;

Zucker, M. B., I. R. Katz, G. J. Thorbecke, D.C. Milot, and J. Holt, 1989, Proc. Natl. Acad. Sci. USA 86: 7571–7574;

Lonky, S. A., J. Marsh, and H. Wohl, 1978, Biochem. Biophys. Res. Commun. 85: 1113–1118;

Katz, I. R., G. J. Thorbecke, B. M. K., J. -z. Yin, D. Clarke, and M. B. Zucker, 1986, Proc. Natl. Acad. Sci. USA 83: 3491–3495;

Gewirtz, A. M., B. Calabretta, B. Rucinski, S. Niewiarowski, and W. Y. Xu, 1989, J. Clin. Invest. 83: 1477–1486;

Han, Z. C., L. Sensebe, J. F. Abgrall, and J. Briere, 1990, Blood 75: 1234–1239.

What is claimed is:

1. A method for neutralizing blood coagulation by administration to a patient in need a pharmaceutically-acceptable formulation comprised of lactoferrin or a polypeptide fragment thereof, comprising residues 1–61.

2. A method of claim 1 wherein said blood coagulation is the result of a heparin-dependent anticoagulation reaction.

3. A method of claim 1 wherein the polypeptide fragment is comprised of a heparin binding site.

4. A method of claim 1 wherein the lactoferrin is human lactoferrin.

5. A method of claim 1 wherein the formulation is administered to a patient that has undergone cardiovascular surgery and other surgical procedures requiring the administration of heparin or its derivatives.

6. A method of claim 1 wherein the formulation is administered to a patient to prolong blood plasma coagulation.

7. A method of claim 1 wherein the formulation is administered to a patient having thrombotic complications associated with inflammatory diseases.

8. A method of claim 1 wherein the formulation is administered to a patient to treat a disorder and/or disease associated with blood coagulation.

* * * * *